US007112653B2

(12) United States Patent
Moore

(10) Patent No.: US 7,112,653 B2
(45) Date of Patent: Sep. 26, 2006

(54) COMPOSITION AND METHOD FOR PRESERVING PROGENITOR CELLS

(75) Inventor: Jeffrey G. Moore, Kennebunkport, ME (US)

(73) Assignee: Inclone Systems, Incorporated, New York, NY (US)

( * ) Notice: Subject to any disclaimer, the term of this patent is extended or adjusted under 35 U.S.C. 154(b) by 0 days.

(21) Appl. No.: 10/737,180

(22) Filed: Dec. 15, 2003

(65) Prior Publication Data

US 2004/0229206 A1 Nov. 18, 2004

Related U.S. Application Data

(63) Continuation of application No. 09/934,251, filed on Aug. 21, 2001, now abandoned, which is a continuation of application No. 09/368,607, filed on Aug. 5, 1999, now Pat. No. 6,280,724, which is a continuation of application No. 08/825,369, filed on Mar. 28, 1997, now Pat. No. 6,084,060, which is a continuation-in-part of application No. 08/762,537, filed on Dec. 9, 1996, now abandoned.

(51) Int. Cl.
*C12N 5/00* (2006.01)

(52) U.S. Cl. .................. 530/200; 424/93.7; 424/185.1; 435/325; 435/366; 514/2; 530/300; 530/350

(58) Field of Classification Search ............... 424/93.7, 424/185.1; 514/2; 530/200, 300, 350; 435/366, 435/325
See application file for complete search history.

(56) References Cited

U.S. PATENT DOCUMENTS

| 4,742,046 A | 5/1988 | Bliah |
| 4,808,611 A | 2/1989 | Cosman |
| 4,985,543 A | 1/1991 | Sugita et al. |
| 5,053,386 A | 10/1991 | Tung |
| 5,186,931 A | 2/1993 | Kishimoto et al. |
| 5,472,867 A | 12/1995 | Kanz et al. |
| 5,545,820 A | 8/1996 | Gatehouse et al. |
| 6,017,527 A | 1/2000 | Maraskovsky et al. |
| 6,084,060 A * | 7/2000 | Moore ..................... 530/200 |
| 6,110,891 A | 8/2000 | Pusztai et al. |
| 6,274,378 B1 | 8/2001 | Steinman et al. |
| 6,280,724 B1 * | 8/2001 | Moore ..................... 424/93.7 |
| 6,310,195 B1 | 10/2001 | Colucci et al. |
| 2003/0049339 A1 | 3/2003 | Colucci et al. |

FOREIGN PATENT DOCUMENTS

| CN | 8510796 | 1/1989 |
| EP | 0173092 | 5/1986 |
| EP | 0337799 | 10/1989 |
| EP | 0942741 B1 | 12/1997 |
| EP | 1009418 B1 | 3/1999 |
| JP | 61/280432 | 12/1986 |
| WO | WO-95/00554 | 1/1995 |
| WO | WO-96/24368 | 8/1996 |
| WO | WO-97/41224 A1 | 11/1997 |
| WO | WO-98/25457 A1 | 6/1998 |
| WO | WO-98/59038 | 12/1998 |
| WO | WO-01/49851 A1 | 7/2001 |

OTHER PUBLICATIONS

U.S. Appl. No. 10/737,180, filed Dec. 15, 2003, Moore.
U.S. Appl. No. 09/476,485, filed Jul. 2000, Colucci et al.
U.S. Appl. No. 09/934,251, filed Aug. 21, 2001, Moore.
Abath FG, *Peptide Research* 3(4): 167-168, 1990.
Altabella, T. et al., "Tobacco Plants Transformed with the Bean αai Gene Express an Inhibitor of Insect α-Amylase in Their Seeds", *Plant Physiol.*, vol. 93, pp. 805-810, 1990.
An, G. et al., "Binary Vectors", *Plant Molecular Biology Manual*, vol. A3, pp. 1-29, 1988.
Arar, C. et al., "ERGIC-53, A Membrande Protein of the Endoplasmic Reticulum-Golgi Intermediate Compartment is Identical to MR60, an Intracellular Mannose-Specific Lectin of Myelomonocytic Cells", *J. Biol. Chem.*, vol. 270, No. 8, pp. 3551-3553, 1995.
Aruffo et al., *Proc. Natl. Acad. Sci. USA*, vol. 84, No. 23, pp. 8573-8577, 1987.
Ausubei et al., *Current Protocols in Molecular Biology*, John Wiley & Sons, NY, NY, 1999.
Bardocz et al., "Intracellular Levels of Polyamines in Krebs II Lymphosarcoma Cells in Mice Fed Phytohaemagglutinin-containing Diets are Coupled with Altered Tumour Growth", *Cancer Letters*, vol. 121, pp. 25-29, 1997.

(Continued)

*Primary Examiner*—Leon B. Lankford, Jr.
(74) *Attorney, Agent, or Firm*—Wilmer Cutler Pickering Hale & Dorr LLP

(57) ABSTRACT

The invention relates to a protein material which is effective to preserve progenitor cells, such as hematopoietic progenitor cells. The protein has an amino acid sequence comprising AQSLSFSFTKFD (SEQ ID NO:1) and a molecular weight of about 12–20 kD, or has an amino acid sequence comprising VVAVEFD (SEQ ID NO:3) and a molecular weight of about 15–20 kD. Heterodimers of the protein are described, and multimers thereof. Methods of using the protein of the invention for preserving progenitor cells in vitro, ex vivo, and in vivo are also described. The invention, therefore, include methods such as myeloablation therapies for cancer treatment wherein myeloid reconstitution is facilitated by means of the specified protein. Other therapeutic utilities are also enabled through the invention, for example, expanding progenitor cell populations ex vivo to increase chances of engraftation, improving conditions for transporting and storing progenitor cells, and facilitated gene therapy to treat and cure a broad range of life-threatening hematologic diseases.

15 Claims, 10 Drawing Sheets

OTHER PUBLICATIONS

Bardocz et al., "Reversible Effect of Phytohaemagglutinin on the Growth and Metabolism of Rat Gastrointestinal Tract", *Gut*, vol. 37, pp. 353-360, 1995.

Bardocz et al., "The effect of phytohaemagglutinin at different dietar concentrations on the growth, body composition and pla insulin of the rat", *British Journal of Nutrition*, vol. 76, pp. 613-626, 1996.

Bardones, S. H. et al., "Bifunctional Properties of Lectins: Lectins Redefined", *Trends in Biochemical Science*, vol. 13, pp. 480-482, 1988.

Bates. EEM et al., "APCs Express DCIR, a Novel C-Type Lectin Surface Receptor Containing an Immunoreceptor Tyrosine-Based Inhibitory Motif", *J. Immunol.*, vol. 163, pp. 1973-1983, 1999.

Bender, AE et al., "Toxicity of Kidney Beans (*Phaseolus vulgaris*) with Particular Reference to Lectins", *Journal of Plant Foods*, vol. 4, pp. 15-22, 1982.

Berardi, A. C. et al., "Functional Isolation and Characterization of Human Hematopoietic Stem Cells", *Science*, vol. 267, pp. 104-108, 1995.

Beuth, J., "Clinical Relevance of Immunoactive Mistletoe Lectin-I", *Anti-Cancer Drugs*, vol. 8 (Suppl. I), pp. 553-555, 1997.

Borge, O. J. et al., "Thrombopoietin, But Not Erythropoietin Promotes Viability and Inhibits Apoptosis of Multipotent Murine Hematopoietic Progenitor Cells In Vitro", *Blood*, vol. 88, No. 8, pp. 2859-2870, 1996.

Caruthers, MD, "Gene Synthesis Machines: DNA Chemistry and its Uses", *Science*, vol. 230, No. 4723, pp. 281-285, 1985.

Clarkson, *Br. J. Rheumatol.*, vol. 3052, pp. 36-39, 1991.

*Clin. Lab. Haem.*, vol. 20, pp. 341-343, 1998.

Coligan et al., *Current Protocols in Immunology*, John Wiley and Sons, NY, NY, 1991.

Coligan et al., *Current Protocols in Immunology*, John Wiley and Sons, NY, NY 1994.

Colucci, G. et al., "cDNA CLoning of FRIL, a Lectin from Dolichos Lablab, that Preserves Hematopoietic Progenitors in Suspension Culture", *Proc. Natl., Acad. Sci.*, vol. 96, pp. 646-650, 1999.

Dallas et al., "The Characterization of an *Escherichia coli* Plasmid Determinant that Encodes for the Production of a Heat-Labile Eneterotoxin", *Plasmids of Medical, Environmental, and Commercial Importance*, Timmis KN and Puehler A. eds., Elsevier/North-Holland Publishing Co., Amsterdam, 1975.

DeLoecker et al., "Effect of Sodium Ascorbate (Vitamin C) and 2-Methyl-1, 4-naphthoquinone (Vitamin $K_3$) Treatment on Human Tumor Cell Growth in *Vitro*. II. Synergism with Combined Chemotherapy Action", *Anticancer Research*, vol. 13, pp. 103-106, 1993.

Denekamp, J., "The Broad Spectrum of Preclinical Radiobiology: British Contributions", *Int. J. Radiation Oncology Biol. Phys.*, vol. 36. No. 2, pp. 497-509, 1996.

Dexter et al., "The Structure of the Hemopoietic Systems", *Cell Biol.*, vol. 3, pp. 428-441, 1987.

Dosil, M. et al., "Mitogenic Signalling and Substrate Specificity of the FIK2/Flt3 Receptor Tyrosine Kinase in Fibroblasts and Interleukin 3-Dependent Hematopoietic Cells", *Molecular and Cellular Biology*, vol. 13, No. 10, pp. 6572-6585, 1993.

Devereux, J. et al., "A Comprehensive Set of Sequence Analysis Programs for the VAX", *NAR*, vol. 12, pp. 387-394, 1984.

Dieckmann, CL et al., *J. Biol. Chem.*, vol. 260, No. 3, pp. 1513-1520, 1985.

Dwek, R. A., "Glycobiology: More Functions for Oligosaccharides", *Science*, vol. 269, pp. 1234-1235, 1995.

Dzionek, A. et al., "EDCA-2, a Novel Plamacytoid Dendritici Cell-specific Type II C-type Lectin, Mediates Antigen Capture and is a Potent Inhibitor of Interferon alpha-beta Induction", *J. Exp. Med.*, vol. 194, pp. 1823-1834, 2002.

Eaton, D. et al., *Biochemistry*, vol. 25, No. 2, pp. 505-512, 1986.

Feng et al., *J. Molec. Evolution*, vol. 25, pp. 351-360, 1987.

Figdor, CG et al., "C-Type Lectin Receptors on Dendritic Cells and Langerhan Cells", *Nature Rev. Immunol.*, vol. 2, pp. 351-360, 1987.

Folk et al., "Increased Survival Time of Leukemic Mice Following Treatment with Phytohemagglutinin", *Experientia*, vol. 27, pp. 444-446, 1971.

Frohman, MA, RACE: Rapid Amplification of cDNA Ends, *PCR Protocols: A Guide to Methods and Applications*, pp. 28-38, Innis MA et al., eds., Academic Press, San Diego, 1990.

Gabius, H. J., "Non-Carbohydrate Binding Partners/Domains of Animal Lectins", *Int. J. Biochem.*, vol. 26, No. 4, pp. 469-477, 1994.

Gabius, HJ et al., eds., *Lectins and Glycogbiology*, Springer-Verlag Inc., New York, 1993.

Gabius, H. J., "Lectinology meets Mythology: Oncological Future for the Mistletoe Lectin?", *Trends in Glycosci and Glycotech*, vol. 6, p. 229, 1994.

Ganguli et al., "A New Approach in Experimental Chemotherapy using Drug-Lectin Combination", *Ind. J. Med. & Ped. Oncol.*, vol. 16, pp. 148-155, 1995.

Gelvin, SB et al., *Plant Molecular Biology Manual*, Kluwer Academic Publishers, Dordrecht, The Netherlands, 1994.

George, DG et al., Macromolecular Sequencing and Synthesis, Selected Methods and Applications, pp. 127-149, 1988, Alan R. Liss, Inc.

Glover, DM et al., *DNA Cloning*, 2d ed., vol. 104, IRL Press, Oxford, 1995.

Gowda et al., "The Complete Primary Structure of a Unique Mannose/Glucose-specific Lectin from Field Bean (Dolichos labgl lab)", *The Journal of Biological Chemistry*, vol. 269, pp. 18789-18793, 1994.

Grant et al., "Purified *Pseudomonas aeruginosa* PA-I Lectin Induces Gut Growth when Orally Ingested by Rats", *FEMS Immunology and Medical Microbiology*, vol. 11, pp. 191-196, 1995.

Gray, MR. et al., "Open Reading Frame Cloning: Identification, Cloning and Expression of Open Reading Frame DNA", *Proc. Natl. Acad. Sci. USA*, vol. 79, p. 6598, 1982.

Greer et al., "Toxicity of Kidney Bean (*Phaseolus vulgaris*) in Rates: Changes in Intestinal Permeability", *Digestion*, vol. 32, pp. 42-46, 1985.

Grunstein, M. et al., "Colony Hybridization: A Method of the Isolation of Cloned DNAs that Contain a Specific Gene", *Proc. Natl. Acad. Sci. USA*, vol. 72, No. 10, pp. 3961-3965, 1975.

Guan et al., *Gene*, vol. 67, pp. 21-30, 1987.

Guigon, M. et al., "Inhibitory Peptides in Hematopoiesis", *Experimental Hematology, US*, New York, NY, vol. 23, No. 6, pp. 477-481, 1995.

Gupta, YP, "Nutritive Value of Soybean", *Intl. J. Trop. Agri..*, vol. 5, No. 3-4, pp. 247-279, 2987.

Hamelryck et al., *J. Molec. Biol.*, vol. 299, pp. 875-883, 2000.

Hames, BD et al., eds., *Gene Probes I and Gene Probes II*, IRL Press, Oxford, 1995.

Hannum, C. O. et al., "Ligand for Flt3/flk2 Receptor Tyrosine Kinase Regulates Growth of Hematopoietic Stem Cells and is Encoded by Variant RNAs", *Nature*, vol. 368, p. 643, 1994.

Hao, Q. L. et al., "Extended Long-Term Culture Reveals a Highly Quiescent and Primitive Human Hematopoietic Progenitor Population", *Blood*, vol. 88, No. 9, pp. 3306-3313, 1996.

Higgins, T. J. V. et al., "The Sequence of a Pea Vicilin Gene and its Expression in Transgenic Tobacco Plants", *Plant Molecular Biology*, vol. 11, pp. 683-695, 1988.

Higgins et al., *CABIOS*, vol. 5, pp. 151-153, 1983.

Higuchi, R. "Recombinant PCR", *PCR Protocols: A Guide to Methods and Applications*, Innis et al., eds., Academic Press, San Diego, pp. 177-183, 1990.

Hoffman, L. M. et al., "Molecular Cloning of *Phaseolus vulgaris* Lectin mRNA and Use of cDNA as a Probe to Estimate Lectin Transcript Levels in Various Tissues", *Nucleic Acids Research*, vol. 10, No. 23, pp. 7820-7829, 1982.

Hopp et al., *Biotechnology*, vol. 6, pp. 1204-1210, 1988.

Horsch, RB et al., "A Simple and General Method for Transferring Genes into Plants", *Science*, vol. 2227, pp. 1229-1231, 1985.

Ijiri et al., "Response of Intenstinal Cells of Differing Topographical and Hierarchical Status to Ten Cytotoxic Drugs and Five Sources of Radiation", *Br. J. Cancer*, vol. 47, pp. 175-185, 1983.

Itakura, K. et al., *Science*, vol. 198, No. 4321, pp. 1056-1063, 1977.

Johnson, KS., *Nature*, vol. 338, No. 6216, pp. 585-587, 1989.

Jones et al., *Nature*, vol. 321 , pp. 522-525, 1986.

Kaufmann, RJ et al., *J. Mol. Biol.*, vol. 159, pp. 601-664, 1982b.

Keller, GH et al., *DNA Probes*, 2d ed., Macmillan Publishers Ltd., England, 1991.
Keil, B. et al., *FEBS Letters*, vol. 56, No. 2, pp. 292-296, 1975.
Kemshead, JT, "Immunomagnetic Manipulation of Hematopoietic Cells: A review of current technology", *International Conference on Metering Apparatus and Tariffs for Electricity Supply*, XX, XX, vol. 1, No. 1, pp. 35-44, XP000613792, 1992.
King, TP et al., "Kidney Bean (*Phaseolus vulgaris*) Lectin-induced Lesions in Rat Small Intestine", *J. Comp. Path.*, vol. 92, pp. 357-373,, 1982.
King, "Kidney Bean (*Phaseolus vulgaris*) Lectin-Induced Lesions in Rat Small Intestine: 1. Light Microscope Studies", *J. Comp. Path.*, vol. 90, pp. 385-395, 1980.
Kollet, O. et al., "The plant lectin FRIL supports prolonged in vitro mainteance of quiescent human cord blood CD34+ CD38 -/Low/ SCID repopulating stem cells", *Experiemental Haemaology*, vol. 28, No. 6, pp. 726-736, Jun. 2000, XP001179365, issn. 030-472X.
Kollet et al., *Blood*, vol. 90, p. 1627a, 1997.
Kollet, O. et al., "Prolonged in Vitro Maintenance of Quiescent Human CD34+/CD38 Stem Cells from Cord Blood by FLT-3 Receptor Interactiving Lectin (FRIL)", *Blood*, vol. 90, No. 10, pp. 365, 1997.
Kuby, J., *Immunology*, WH Freeman & Co., NY, p. 95, 1992.
Kuriyama, M. et al., "Identification of AF-6 and Canoe as Putative Targets for Ras", *The Journal of Biological Chemistry*, vol. 271, No. 2, pp. 607-610, 1996.
Kuttan et al., "Reduction of Leukopenia in Mice by <Viscum Album> Administration during Radiation and Chemotheraphy", *Tumori*, vol. 79, pp. 74-76, 1983.
Laemmli, U.K., "Cleavage of Strctural Proteins During the Assembly of the Head of Bacteriophage T4", *Nature*, pp. 680-685, 1970.
Leary, J.J. et al., "Rapid and Sensitive Colorimetric Method for Visualizing Biotin-Ibaled DNA Probes Hybridized to DNA or RNA Immobiled on Nitrocellulose: Bio-blots:", *Proc. Natl. Acad. Sci USA*, vol. 80, p. 4045, 1983.
Lenartz et al., "Immunoprotective Activity of the Galactoside-Specific Lectin from Mistletow after Tumor Destructive Therapy in Glioma Patients", *Anticancer Research*, vol. 16, pp. 3799-3802, 1996.
Lenfant, J. et al. "Inhibitor of Hematopoietic Pluripotent Stem Cell Proliferation: Purification and Determination of its Structure", *Proc. of the Nat. Acad. of Sci. USA*, vol. 86, pp. 779-782, 1989.
Liener, IE et al., "Starch blockers: a potential source of trypsin inhibitors and lectins", *The American Journal of Clinical Nutrition*, vol. 39, pp. 196-200, Feb. 1984.
Liener, IE, "Implications of Antinutritional Components in Soybeah Foods", *Crit. Rev. Food Sci. Nutrit.*, vol. 34, No. 1, pp. 31-67, 1994.
Liu et al., *Nat. Immunol.*, vol. 2, No. 7, pp. 585-589, 2001.
Lyman, S. D. et al., "Molecular Cloning of a Ligand for the Flt3/flk2 Tyrosine Kinase Receptor: a Proliferative Assay for Primitive Hematopoietic Cells", *Cell*, vol. 74, p. 1157, 1993.
Maina, CV et al., *Gene*, vol. 74, pp. 36-373, 1988.
Marfatia, S. M. et al., "Identification of the Protein 4.1 Binding Interface on Glycophorin C and p55, a Hmologue of the Drosphila discs-large Tumor Supperessor Protein", *The Journal of Biological Chemistry*, vol. 270, No. 2, pp. 715-719, 1995.
Marston et al., "Solubilization of Protein Aggregates", *Guide to Protein Purification*, pp. 266-267, 1990, Deutscher MP, ed.., Academic Press, San Diego.
Marston, "The Purification of Eukaryotic Proteins Express in *E. coli*", *DNA Cloning*, Glover DM ed., vol. III, IRL Press, Ltd., Oxford, 1987.
Marx, *Science*, vol. 229, pp. 455-456, 1985.
McPherson, MJ ed., *Directed Mutagenesis: A Practical Approach*, IRL Press, Oxford, 1991.
Meinkoth, J. et al., Hybridization of Nucleic Acids Immobiled on Solid Supports:, *Anal. Biochem.*, vol. 138, No. 2, p. 267, 1984.
Mekori et al., "Further Observations on the Effect of pHA in Conjuction with Radiotherapy and Chemotherapy on S-180 in Swiss Mice", *Europ. J. Cancer*, vol. 10, pp. 67-74, 1974.
Mikayama et al., "Molecular cloning and functional expression of a cDNA encoding glycoslyation-inhibiting factor", *PNAS*, vol. 90, pp. 10056-10060, 1993.

Mo, H. et al., "Purification and characterization of *Dolichols Lablab* lectin", *Glycobiology*, vol. 9, No. 2, pp. 173-179, 1999.
Mody et al., "Use of Lectins as Diagnostic and Therapeutic Tools for Cancer", *Journal of Pharmacological and Toxicological Methods*, vol. 33, pp. 1-10, 1995.
Moore, A.J.G. et al., "A new lectin red kidney beans called PvFRIL stimulates proliferation of NIH 3T3 cells expressing the Flt3 receptor", *BBA-General Subjects*, Elsevier Science Publishers, NL vol. 1475, No. 3, pp. 216-224, Jul. 26, 2000.
Moore et al., *Biochem. Biophys. Acta*, vol. 25027, pp. 1-9, 2000.
Moore et al., *Blood*, vol. 90, p. 308, 1997.
Moore et al., *Blood*, vol. 90. p. 1366a, 1997.
Moore, JG et al., "Preservation of Hematopoietic Progenitors for Prolonged Periods in Suspension Cultures by Flk2/flt3 Receptor-Interacting Lectin (FRIL) a new Lectin Identified in Red Kidney Beans", *Blood*, vol. 90, p. 428A, 1997.
Moreno J. et al., "A Lectin Gene Encodes for the α-amylase Inhibitor of the Common Bean", *PNAS*, vol. 86, pp. 7885-7889, 1989.
Mosmann, T., "Rapid Colorimetric Assay for Cellular Growth and Survival: Application to Proliferation and Cytotoxicity Assays", *Journal of Immunological Methods*, vol. 65, pp. 55-63, 1983.
Nagai, K. et al., *Methods Enzymol.*, vol. 153, pp. 461-481, 1987.
Ngo et al., The Protein Folding Problem and Tertiary Structure Prediction, pp. 433 and 492-495, 1994, Birkhauser, Boston.
Ogawa, M., "Differentiation and Proliferation of Hematopoietic Stem Cells", *Blood*, vol. 87, p. 2855, 1993.
Okuda et al., "Use of Phytohemagglutinin in the Treatment of Maxillary Cancer", *Arch Otorhinolaryngol*, vol. 228, pp. 127-134, 1980.
Opdenakker, C., et al., "Cells Regulate the Activities of Cytokines by Glycosylation", *The FASEB Journal*, vol. 9, pp. 453-457, 1995.
Pawloski, K. et al., "Isolation of Total, Poly(A+) and Polysomal RNA from Plant Tissues", *Mol. Plant Biol. Manual*, vol. 5, pp. 1-13, 1994.
Pearson et al., "Improved Tools for Biological Sequence Comparison", *Proc. Natl., Acad. Sci. USA*, vol. 85, pp. 2444-2448, 1988.
Peltzer, A. I. et al., "Self-renewal of Primitive Human Hematopoietic Cells (long-term-culture-initiating cells) in vitro and Their Expansion in Defined Medium", *Proc. Natl. Acad. Sci. (USA)*, vol. 93, pp. 1470-1474, 1996.
Pryme et al., "Phytohemagglutinin-induced gut hyperplasia and the growth of a mouse lymphosarcoma tumor", *Journal of Experiemental Therapeutics & Oncology*, vol. 2, pp. 171-176, 1996.
Pryme et al., "The effect of switching between a phytohemagglutinin-containing and a control diet on the growth and lipid content of a Krebs II lymphosarcoma tumor", *Journal of Experimental Therapeutics & Oncology*, vol. 1, pp. 273-277, 1996.
Pueyo, J. J. et al., "Degredation of Transport-Competent Destablished Phaseolin with a Signal of Retention in the Endoplasmic Reticulum Occurs in the Vacuole", *Planta*, vol. 196, pp. 586-596, 1995.
Pusztai, "Characteristics and consequences of interactions of lectins with the intestinal mucosa", *Archiivos Latino Americanos de Nutricion*, vol. 44, No. 4-S. pp. 10S-15S.
Pusztai et al., "Dietary Lectins as Extraneous Metabolic Signals", *Biological Effects of Lectins*, vol. 9, pp. 131-138, 1993.
Pusztai, "Dietary lectins are metabolic signals for the gut and modulate immune and hormone functions", *Euopean Journal of Clinical Nutrition*, vol. 47, pp. 691-699, 1993.
Pusztai, A. et al., *Lectins: Biomedical Perspectives*, Taylor & Francis, London, 1995.
Pusztai et al., "Novel Dietary Strategy for Overcoming the Antinutritional Effects of Soyabean Whey of High Agglutinin Content", *British Journal of Nutrition*, vol. 77, pp. 933-945, 1997.
Reichman et al., *Nature*, vol. 332, pp. 323-327, 1988.
Renz, J. et al., "A Colorimetric Method for DNA Hybridization", *Nucleic Acids Res.*, vol. 12, p. 3435, 1984.
Richardson et al., *Nucleic Acids Res.*, vol. 11, p. 6167, 1983.
Richter et al., "The Action of Phytohemagglutinin in Rabbits", *Int. Arch. Allergy*, vol. 35, pp. 417-433, 1969.
Riggs, P. et al., eds., *Current Protocols in Molecular Biology*, Greene Associates/Wiley Interscience, New York, 1990.

Robinson et al., "Combinations of the Effect of Radiotherapy, Alkylating Agents and Phytohemagglutinin on Sarcoma 180 in Swiss Miss", *Europ. J. Cancer*, vol. 9, pp. 125-131, 1973.

Rodhouse, JC et al., "Red kidney bean poisoning in the UK: an analysis of 50 suspected incidents between 1976 and 1989", *Epidemiol. Infect.*, vol. 105, pp. 485-491, 1990.

Rodwell, *Nature*, vol. 342, pp. 99-100, 1989.

Roehm, NW et al., "An Improved Colorimetric Assay for Cell Proliferation and Viability Utilizing the Tetrazolium Salt XTT", *J. Immunol. Methods*, vol. 142, No. 2, pp. 257-265, 1991.

Rubinstein et al., *Prox. Natl. Acad. Sci*, vol. 92, pp. 10119-10122, 1995.

Saiki, RK et al., *Science*, vol. 239, p. 487, 1988.

Sambrook, J. et al., *Molecular Cloning: A Laboratory Manual*, 2d ed, Cold Spring Harbor Laboratoary, Cold Spring Harbor, 1989.

Santin et al., *Obstet. Gynecol.*, vol. 96, No. 3, pp. 422-430, 2000.

Scahill, SJ et al., "Expression and Characterization of the Product of a Human Immune Interferon DNA Gene in Chinese Hamster Ovary Cells", *Proc. Natl. Acad. Sci USA*, vol. 80, pp. 4654-4659, 1993.

Schon et al., *J. Reprod. Immunol.*, vol. 50, No. 2, pp. 87-104, 2001.

Schrek et al., "Radioresistance of Phytohemagglutinin-Treated Normal and Leukemic Lymphocytes", *J. Natl. Cancer Inst.*, vol. 32, pp. 507-521, 1964.

Shah, A. J. et al., "Flt3 Ligand Induces Proliferaton of Quiescent Human Bone Marrow CD34 CD38 Cells and Maintains Progenitor Cells In Vitro", *Blood*, vol. 9, pp. 3563-3570, 1996.

Sharon N. et al., "Lectins as Cell Recognition Molecules", *Science*, vol. 246, pp. 227-234, 1989.

Small, D. et al., "STK-1, the Human Hmolog of Flk-2/Flt-3, is Selectively Expressed in CD34 Human Bone Marrow Cells and is Involved in the Proliferation of Early Progenitor/Stem Cells", *PNAS*, vol. 91, pp. 459-463, 1994.

Smith, DB, *Gene*, vol. 67, pp. 31-40, 1988.

Smith, LM et al., *Nucleic Acids Res.*, vol. 13, p. 2399, 1985.

Southern, PJ et al., *J. Mol. Appl. Genet.*, vol. 1, pp. 327-341, 1982.

Spangrude, G. J. et al., "Purification and Characterization of Mouse Hematopoietic Stem Cells", *Science*, vol. 241, pp. 58-62, 1991.

Steinman, *Annu,. Rev. Immunol.*, vol. 9, pp. 271-296, 1991.

Stengelin et al., *EMBO J.*, vol. 7, No. 4, pp. 1053-1059, 1988.

Stubbs, ME et al., "Production of Pea Lectin in *Escherichia coli*", *J. Biol. Chem.*, vol. 261, No. 14, pp. 6141-6144, 1986.

SU et al., "Hematopoietic Stem Cell-Based Gene Therapy . . . ", *Blood*, vol. 87, No. 7, pp. 2283-2290, 1997.

Subramani, S. et al., *Mol., Cell Biol.*, vol. 1, pp. 854-864, 1981.

Tchernychev, B. et al., "Natural Human Antibodies to Dietary Lectins", *FEBS Letters*, vol. 397, pp. 139-141, 1996.

Tessler, S. et al., "Heparin Modulates the Interaction if VEGF 165 with Soluble and Cell Associated flk-1 Receptors", *The Journal of Biological Chemistry*, vol. 269, No. 17, pp. 12456-12461, 1994.

Turhan, A. G. et al., "Clonal Hematopoiesis Demonstrated by X-Linked DNA Polymorphisms After Allogeneic Bone Marrow Transplantation", *The New England Journal of Medicine*, vol. 320, No. 25, pp. 1655-1661, 1989.

Turley et al., *Science*, vol. 288, pp. 522-527, 2000.

Uhlen, M. et al., *Gene*, vol. 23, pp. 369-378, 1983.

Ullman, *Gene*, vol. 29, pp. 27-31, 1984.

Unkeless, J. C., "Characterization of a Monoclonal Antibody Directed Against Mouse Macrophace and Lymphocyte Fc Receptors", *J. Exp. Med.*, vol. 150, pp. 580-596, 1979.

Urlaub, G. et al., *Proc. Natl. Acad. Sci USA*, vol. 77, pp. 4216-4220, 1980.

Van Damme, EJ et al., "A Molecular Cloning of the Bark and Seed Lectins from the Japanesegoda Tree (*Sophora japonica*)", *Plant Mol. Biol.*, vol. 33, No. 3, pp. 523-536, 1997.

Van Damme, EJM et al., "A Lectin and a Lectin-Related Protein are the Two Most Prominent Proteins in the Bark of Yellow Wood (*Clastrasis luteau*)", *Plant Mol. Biol.*, vol. 29, No. 3, pp. 579-598, 1995.

Van Eijsden, RR et al., "Mutational Analysis of Pea Lectin: Substitution of Asn125 for Asp in the Monosaccharide-Binding Site Eliminates Mannose/Glucose-Binding Activity", *Plant Mol. Biol.*, vol. 20, No. 6, pp. 1049-1058, 1992.

Van Etten, RA et al., *Cell*, vol. 58, pp. 669-678, 1989.

Verhoeyen et al., *Science*, vol. 239, pp. 1534-1560, 1988.

Wang, Q. et al., "Identification of intact peanture lectin in peripheral venous blood", *The Lancet*, vol. 352, pp. 1831-1832, 1998.

Wimer, B., "Therapeutic activities of PHA-L4, the mitogenic isolectin of phytohemagglutinin", *Mol. Biother.*, vol. 2, pp. 74-90, Jun. 1990.

Young, J. C. et al., "Retention of Quiescent Hematopoietic Cells with High Proliferative Potential During Ex Vivo Stem Cell Culture", *Blood*, vol. 87, No. 2, pp. 545-556, 1996.

Yu, et al., "Reversible Inhibition of Proliferation of Epithelial Cell Lines by *Agaricus bisporus* (edible mushrooms) Lectin", *Cancer Res.*, vol. 53, pp. 4627-4632, 1993.

Zipori, D., "Regulation of Hemopoiesis by Cytokines that Restrict Options for Growth and Differentiation", *Cancer Cells*, vol. 2, No. 7, pp. 205-211, 1990.

Zipori, D., "The Renewal and Differentiation of Hemopoietic Stem Cells", *The FASEB Journal*, vol. 6, pp. 2691-2697, 1992.

Zoller, MJ, *Methods Enzymol.*, vol. 100, 99, 468-500, 1983.

Zoller, MJ *DNA*, vol. 3, pp. 479-488, 1984.

Zoller, MJ et al., *Nucleic Acids Res.*, vol. 10, pp. 6487-6500, 1982.

Greenberg, P. L., "Immunologic Selection of Hemopoietic Precursor Cells Utilizing Antibody-Mediated Plate Binding", *Blood*, vol. 65, pp. 190-197, 1985.

Karsunky, H., "Flt3 Ligand Regulated Dendritic Cell Development from Flt3+ Lymphoid and Myeloid-committed Progenitors to Flt3+ Dendritic Cells In Vivo", *J. Exp. Med.*, vol. 198 (2), pp. 305-313, 2003.

Steinman, R. M., "Some Interfaces of Dendritic Cell Biology", *APMIS*, vol. 111, pp. 675-697, 2003.

* cited by examiner

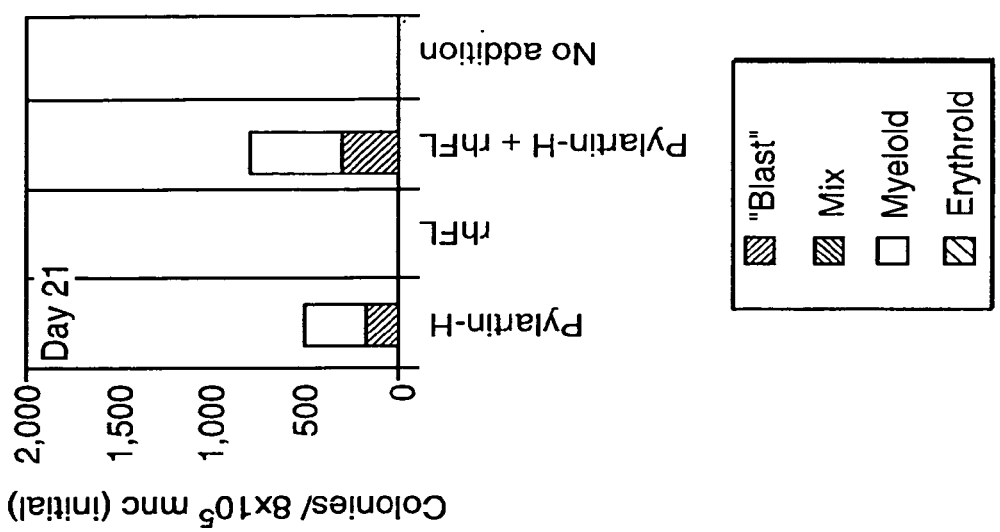
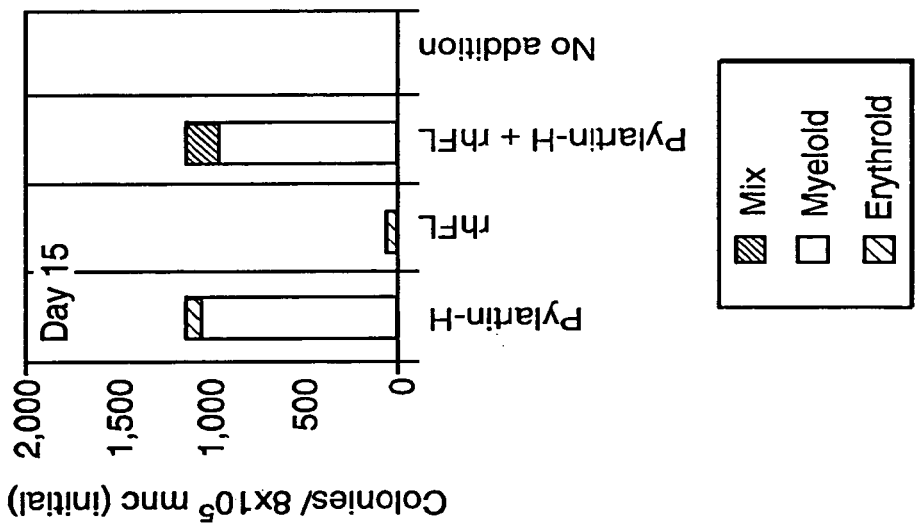
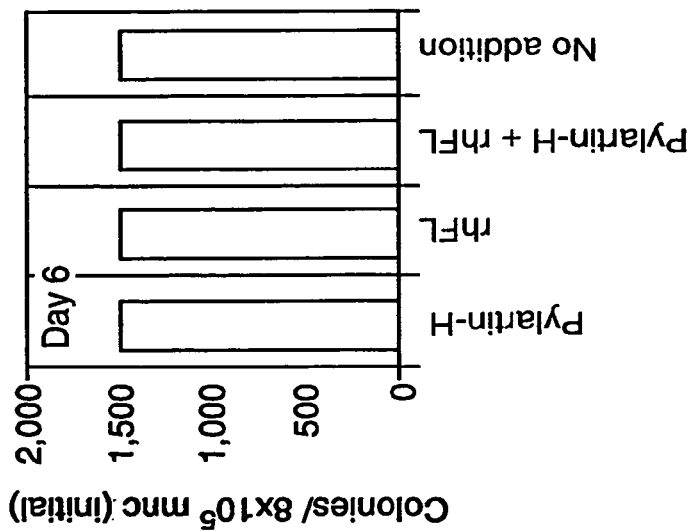

SEQUENCE LISTING

<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: peptide chain of pylartin protein

<400> SEQUENCE: 1

Ala Gln Ser Leu Ser Phe Ser Phe Thr Lys Phe Asp
 1               5                  10

<210> SEQ ID NO 2
<211> LENGTH: 14
<212> TYPE: PRT
<213> ORGANISM: Artificial Sequence
<220> FEATURE:
<223> OTHER INFORMATION: beta peptide sequence

<400> SEQUENCE: 2

Ala Gln Ser Leu Ser Phe Ser Phe Thr Lys Phe Asp Leu Asp
 1               5                  10

<210> SEQ ID NO 3
<211> LENGTH: 7
<212> TYPE: PRT
<213> ORGANISM: Artificial Sequence
<220> FEATURE:
<223> OTHER INFORMATION: alpha peptide sequence

<400> SEQUENCE: 3

Val Val Ala Val Glu Phe Asp
 1               5

<210> SEQ ID NO 4
<211> LENGTH: 11
<212> TYPE: PRT
<213> ORGANISM: Artificial Sequence
<220> FEATURE:
<223> OTHER INFORMATION: alpha peptide sequence

<400> SEQUENCE: 4

Thr Asp Ser Tyr Val Val Ala Val Glu Phe Asp
 1               5                  10

US 7,112,653 B2

COMPOSITION AND METHOD FOR PRESERVING PROGENITOR CELLS

This is a continuation-in-part of application Ser. No. 08/762,537, filed on Dec. 9, 1996 now abandoned.

BACKGROUND OF THE INVENTION

The invention relates to an agent and method for use in connection with progenitor cells. More specifically, the invention relates to a protein capable of preserving progenitor cells and a method of using the protein for maintaining and preserving progenitor cells.

Each day the bone marrow generates and releases into the circulation several billion fully-differentiated, functional blood cells. Production of these cells derives from a small stock of quiescent progenitor cells (including the most primitive stem cells and other less primitive but still immature progenitors) by a process called hematopoiesis (Zipori 1992). The most primitive stem cells have the capacity to generate >$10^{13}$ cells containing all blood lineages (Turhan et al. 1989). The production of such a large number of cells is achieved by extensive proliferation coupled with successive differentiation steps leading to a balanced production of mature cells. Progenitor cells progressively lose their capacity to generate multiple cells lineages and eventually produce cells of one or two cell lineages.

Soluble regulators and cell-cell interactions mediate differentiation directions of immature progenitors through a tightly-controlled but inadequately understood process. Several of the body's soluble factors have been isolated and characterized both in culture and in animals (see, e.g., Ogawa (1993) and references therein). Regulators such as the colony stimulating factors (e.g., IL3, GM-CSF, G-CSF, M-CSF) not only induce proliferation and differentiation of progenitors capable of producing cells of either multiple cell lineages (IL3 and GM-CSF) or single cell lineages (G-CSF and M-CSF), but also maintain viability of their respective progenitors. Other regulators such as interleukin-1 (IL1), the kit ligand (KL), and thrombopoietin (Borge et al. 1996) increase viability of multipotential progenitors in addition to other functions. No known cytokines alone or in combination can maintain viability of primitive progenitors in liquid culture without stromal support beyond a few days.

Regulation of primitive stem cells appears to differ from that of immature, multilineage progenitors. Stem cells are primarily quiescent and do not appear to respond immediately to regulators that induce proliferation and differentiation. Maintenance of these cells in the body is mediated via cell-cell interactions and soluble regulators. Maintenance of quiescent stem cells in vitro has been achieved by culturing cells on adherent stromal layers with soluble regulators such as IL3, IL6, KL and LIF (Young et al. 1996). Recently, the addition of FL to this complex culture has been found to extend maintenance of quiescent stem cells from a few weeks to three months (Shah et al. 1996). Establishing stromal cells cultures is not easily applicable to clinical settings.

Lectins, defined as carbohydrate-binding proteins other than antibodies or enzymes, (Baronedes 1988), are widespread among plants, prokaryotes, and eukaryotes. Each lectin recognizes a specific carbohydrate moiety, and forms a non-covalent bond with the carbohydrate through a stereochemical fit of complementary molecules (e.g., hydrophobic pocket). Carbohydrates are widely present on cell surfaces (in the forms of glycoproteins, glycolipids, and polysaccharides), and appear to mediate cell-cell contacts including cell recognition (Sharon et al. 1989). Abnormal glycosylation patterns are associated with disease by causing alterations in a protein's conformation, stability, or protease resistance (Dwek 1995).

Gowda et al. (1994) describe the isolation of a mannose-glucose-specific lectin from the hyacinth bean (*Dolichos lab lab*). Purification and sequencing of this lectin is said to indicate that the protein includes two nonidentical subunits. The Gowda et al. publication describes evolutionary relationships of the lectin to other lectins, but does not ascribe any function to the protein beyond saccharide-binding in the plant source.

Cell agglutinating properties of certain plant lectins have been known for over 100 years. Certain lectins have been used as tools in immunology laboratories as potent, specific activators of T lymphocytes (phytohemagglutinin (PHA) and concanavalin A (ConA)) and B lymphocytes (pokeweed mitogen (PWM)) for over 30 years (Sharon et al. 1989). Some lectins have also been used to isolate hematopoietic progenitors for over 15 years (Gabius 1994a). Large numbers of cancer patients in Europe have received mistletoe lectin (*Viscum album*) intravenously as a candidate cancer therapy without major complications (Gabius 1994b). Whether these plant lectins act on mammalian cells via de novo means, or simply mimic their functional mammalian homologs is not yet known. No lectin has yet been successfully developed as a human therapeutic.

In view of the above considerations, it is clear that regulation of the hematopoietic process remains incompletely understood. Most soluble regulators identified, such as the colony stimulating factors and interleukins, induce proliferation and differentiation of progenitors cells in culture and their levels in the blood circulation increase during times of hematopoietic stress (e.g., blood loss, infection). For example, U.S. Pat. No. 4,808,611 describes a method of using IL1 and a colony stimulating factor to induce proliferation and differentiation of hemopoietic stem cells. Some soluble regulators, such as IL1, IL6, KL, FL, and Tpo, appear to provide increase viability of stem cells without directly affecting proliferation and differentiation. But no known soluble regulators, alone or in combination, have yet been reported that enable maintenance and amplification of stem cells populations in vitro without stromal cells. As a consequence, numerous potential therapeutic approaches to diseases such as cancer and genetic blood diseases remain unavailable.

Accordingly, it is one of the purposes of this invention to overcome the above limitations in methods of regulating hematopoietic processes, by providing a factor and method of protecting, maintaining, and expanding hematopoietic progenitor cell populations. It is another purpose of the invention to provide means for protecting the integrity of the hematopoietic processes in vivo as an adjunct to therapeutic treatments related to cancer and other diseases which can otherwise adversely impact upon the hematopoietic system.

SUMMARY OF THE INVENTION

It has now been discovered that these and other objectives can be achieved by the present invention, which provides a protein which preserves progenitor cells and a method of using the protein. The protein has an amino acid sequence comprising AQSLSFSFTKFD (SEQ ID NO:1) and a molecular weight of about 12–20 kD, or has an amino acid sequence comprising VVAVEFD (SEQ ID NO:3) and a molecular weight of about 15–20 kD. The method of preserving progenitor cells comprises contacting progenitor cells with a protein having an amino acid sequence comprising AQSLSFSFTKFD (SEQ ID NO:1) and a molecular weight of about 12–20 kD, or having an amino acid sequence comprising VVAVEFD (SEQ ID NO:3) and a molecular weight of about 15–20 kD, in an amount sufficient to preserve the progenitor cells.

In one embodiment, the invention includes a method of treating a mammal in need of hematopoietic therapy. Here the method comprises:

a) obtaining a tissue sample from the mammal, the tissue sample comprising hematopoietic progenitor cells;

b) culturing the progenitor cells in the presence of a protein which preserves the progenitor cells, to provide cultured cells enriched in the progenitor cells, wherein the protein has an amino acid sequence comprising AQSLSFSFTKFD (SEQ ID NO:1) and a molecular weight of about 12–20 kD, or has an amino acid sequence comprising VVAVEFD (SEQ ID NO:3) and a molecular weight of about 15–20 kD;

c) subjecting the mammal to conditions sufficient to effect myeloablation; and d) administering the cultured cells to the mammal following the myeloablation to reconstitute the hematopoietic system of the mammal.

In an alternative embodiment, the invention includes a method of enriching progenitor cells. The method comprises culturing progenitor cells in a progenitor-preserving amount of a protein having an amino acid sequence comprising VVAVEFD (SEQ ID NO:3) and a molecular weight of about 15–20 kD, or having an amino acid sequence comprising AQSLSFSFTKFD (SEQ ID NO:1) and a molecular weight of about 12–20 kD, wherein the protein specifically preserves the progenitor cells, and wherein the culturing is performed under conditions permitting preservation of progenitor cells while permitting the number of differentiated cells to decrease.

In still another embodiment, the invention includes a method of improving hematopoietic competence in a mammal. In this case, the method comprises:

a) culturing a tissue sample comprising hematopoietic progenitor cells in a growth medium containing a protein having an amino acid sequence comprising AQSLSFSFTKFD (SEQ ID NO:1) and a molecular weight of about 12–20 kD, or having an amino acid sequence comprising VVAVEFD (SEQ ID NO:3) and a molecular weight of about 15–20 kD, in an amount sufficient to preserve the progenitor cells and to provide cultured cells enriched in the progenitor cells; and b) transfusing the enriched cultured cells to the mammal to provide progenitor cells for generating blood cellular components in the mammal.

In yet another embodiment, the invention further includes a method of transfecting an exogenous DNA sequence into somatic cells, which includes the improvement comprising transfecting progenitor cells selectively preserved by a protein having an amino acid sequence comprising AQSLSFSFTKFD (SEQ ID NO:1) and a molecular weight of about 12–20 kD, or having an amino acid sequence comprising VVAVEFD (SEQ ID NO:3) and a molecular weight of about 15–20 kD.

In a further embodiment, the invention includes a composition for maintaining viability of progenitor cells ex vivo, comprising a cell growth medium and a protein which preserves progenitor cells, wherein the protein has an amino acid sequence comprising AQSLSFSFTKFD (SEQ ID NO:1) and a molecular weight of about 12–20 kD, or has an amino acid sequence comprising VVAVEFD (SEQ ID NO:3) and a molecular weight of about 15–20 kD.

Moreover, in yet another embodiment, the invention includes, a method for preserving progenitor cells in a mammal. The method of this embodiment comprises:

a) administering to the mammal a protein which specifically preserves progenitor cells, the protein having an amino acid sequence comprising AQSLSFSFTKFD (SEQ ID NO:1) and a molecular weight of about 12–20 kD, or having an amino acid sequence comprising VVAVEFD (SEQ ID NO:3) and a molecular weight of about 15–20 kD, in an amount sufficient to preserve progenitor cells of the mammal in a substantially non-proliferative state;

b) exposing the mammal to myeloablative conditions sufficient to effect ablation of proliferating myeloid cells but sparing non-proliferating progenitor cells; and c) following the exposing, reestablishing proliferation or differentiation of the preserved progenitor cells.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawings, wherein:

FIGS. 8A–8C are a set of histograms showing that the protein of the invention, and not FL, preserves primitive hematopoietic progenitor cells in liquid culture after 15 and 21 days.

DETAILED DESCRIPTION OF THE PREFERRED EMBODIMENTS

Figure 1:
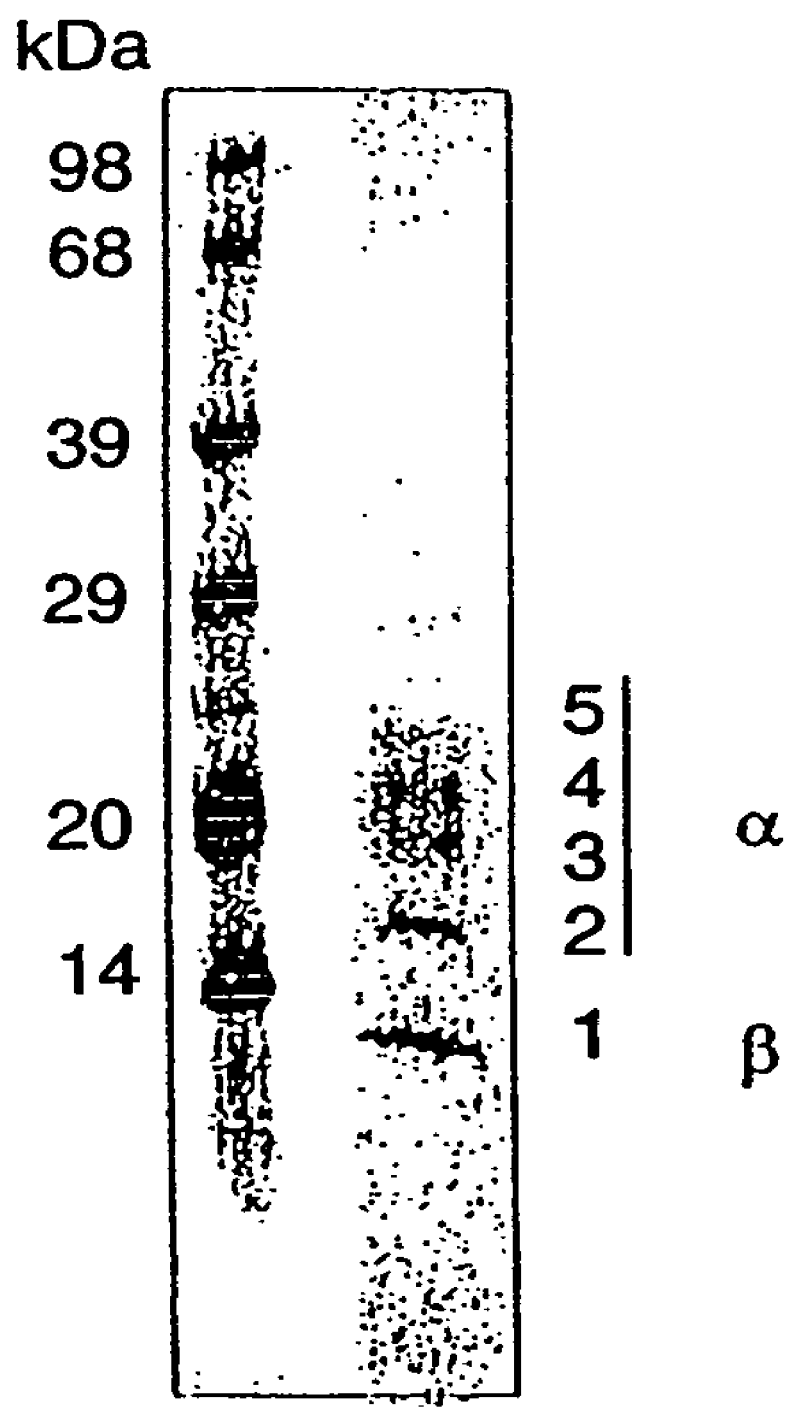
FIG. 1 shows an electrophoretic separation of protein illustrating the alpha and beta subunit structure of the pylartin protein obtained from hyacinth beans.
Figure 2:
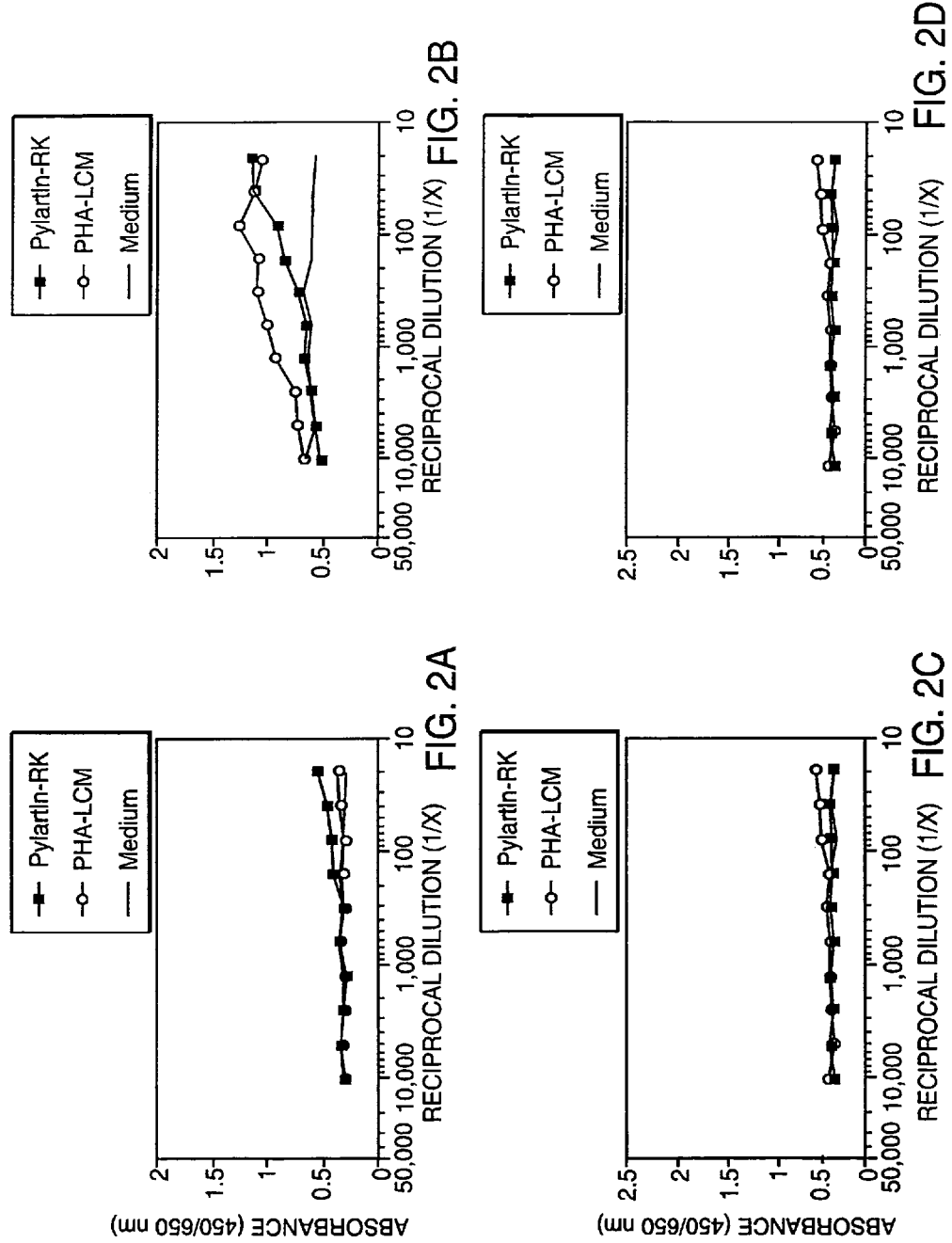
FIG. 2A is a graph of the effect of the protein of the invention on flk2-transfected 3T3 cells in the presence of IL1.
FIG. 2B is a graph of the effect of the protein of the invention on flk2-transfected 3T3 cells in the absence of IL1.
FIG. 2C is a graph of the effect of the protein of the invention on untransfected 3T3 cells in the presence of IL1.
FIG. 2D is a graph of the effect of the protein of the invention on untransfected 3T3 cells in the absence of IL1.

The present invention is directed to a protein which preserves progenitor cells, and a method for use of the protein in preserving and maintaining progenitor cells. By "protein" is meant any isolated natural or synthetic oligo- or polypeptide comprising a sequence of amino acid residues linked by peptide bonds.

As used herein, "progenitor cell" refers to any somatic cell which has the capacity to generate fully differentiated, functional progeny by differentiation and proliferation. Progenitor cells include progenitors from any tissue or organ system, including, but not limited to, blood, nerve, muscle, skin, gut, bone, kidney, liver, pancreas, thymus, and the like. Progenitor cells are distinguished from "differentiated cells," which are defined as those cells which may or may not have the capacity to proliferate, i.e., self-replicate, but which are unable to undergo further differentiation to a different cell type under normal physiological conditions. Moreover, progenitor cells are further distinguished from abnormal cells such as cancer cells, especially leukemia cells, which proliferate (self-replicate) but which generally do not further differentiate, despite appearing to be immature or undifferentiated.

Progenitor cells include all the cells in a lineage of differentiation and proliferation prior to the most differentiated or the fully mature cell. Thus, for example, progenitors include the skin progenitor in the mature individual, which is capable of differentiation to only one type of cell, but which is itself not fully mature or fully differentiated. Production of mature, functional blood cells results from proliferation and differentiation of "unipotential progenitors," i.e., those progenitors which have the capacity to make only one type of one type of blood cell. For red blood cell production, a progenitor called a "CFU-E" (colony forming unit-erythroid) has the capacity to generate two to 32 progeny cells.

Various other hematopoietic progenitors have been characterized. For example, hematopoietic progenitor cells include those cells which are capable of successive cycles of differentiating and proliferating to yield up to eight different mature hematopoietic cell lineages. At the most primitive or undifferentiated end of the hematopoietic spectrum, hematopoietic progenitor cells include the hematopoietic "stem cells." These rare cells, which represent 1 in 10,000 to 1 in 100,000 of cells in the bone marrow, each have the capacity to generate $>10^{13}$ mature blood cells of all lineages and are responsible for sustaining blood cell production over the life of an animal. They reside in the marrow primarily in a quiescent state and may form identical daughter cells through a process called self-renewal. Accordingly, such an uncommitted progenitor can be described as being "totipotent," i.e., both necessary and sufficient for generating all types of mature blood cells. Progenitor cells which retain a capacity to generate all blood cell lineages but which can not self-renew are termed "pluripotent." Cells which can produce some but not all blood lineages and can not self-renew are termed "multipotent."

The protein of the invention is useful to preserve any of these progenitor cells, including unipotent progenitor cells, pluripotent progenitor cells, and/or totipotent progenitor cells. The protein has demonstrated particular efficacy in preserving hematopoietic progenitor cells, however, the protein can be used to preserve progenitor cells of other tissues such as those mentioned above. Because of its properties in controlling the hematopoietic process, the protein of the invention is also referred to herein as "pylartin" or "the pylartin protein." However, it should be recognized that the protein is also useful in the preservation and maintenance of progenitor cells in non-hematopoietic tissues.

The pylartin protein is especially useful in preserving hematopoietic progenitors in mammals such as humans, mice, rats, etc. In the human, primitive mature hematopoietic progenitor cells can be identified as belonging to a class of cells defined by their expression of a cell surface antigen designated CD34. These cells may be referred to as $CD34^+$ cells. In the mouse, hematopoietic progenitor cells may be referred to as $Sca^+Lin^-$ cells, reflecting their cell surface antigen signature. Other mammalian species exhibit similar signature properties identifying hematopoietic progenitor cells. Hematopoietic progenitors can also be identified by their expression of the flk2/flt3 receptor.

Human hematopoietic progenitor cells which express the CD34 antigen and/or the flk2 receptor are referred to herein as "primitive progenitor cells." By contrast, hematopoietic cells which do not express either the CD34 antigen or the flk2 receptor are referred to as "mature progenitor cells."

Generally, the pylartin protein is effective to preserve progenitor cells which express the CD34 antigen, or the flk2 receptor. The progenitor cells can include cells modified to express the CD34 antigen or flk2 receptors on their surface. In a preferred case, the protein has significant binding affinity for flk2 receptor on the cells, wherein binding of the protein with the flk2 receptor mediates the inhibition of differentiation of the cells.

The pylartin protein mediates a "preservation" of progenitor cells. By this is meant that the peptide either inhibits differentiation of the progenitor cells, or induces their proliferation without differentiation. In particular, by inhibiting differentiation processes, it is to be understood that the peptide significantly lowers the rate at which cells differentiate, and it may in fact completely stop these processes by possibly maintaining progenitor cells in a quiescent or G0 state of the cell cycle. However, the protein does so without killing the cells in significant numbers. In this sense, pylartin is significantly distinguished from factors which inhibit or interfere with cellular processes (e.g., DNA replication, protein synthesis), and which thereby induce significant cell mortality.

The pylartin protein of the invention can be obtained from a natural source, namely being derived from a legume. A legume is a fruit or seed (e.g., a pea or bean) of a leguminous plant, which are plants from a family (*Leguminosae*) of dicotyledonous herbs, shrubs, and trees bearing (nitrogen-fixing bacteria) nodules on their roots. More specifically, the pylartin protein can be obtained from members of the tribe

*Phaseoleae*. In particular, the protein can be obtained from hyacinth beans (*Dolichos lab lab*), kidney beans, e.g., red kidney beans (*Phaseolus vulgaris*), or the black-eyed pea (*Vigna senensis*). In its native form obtained from such natural sources, the protein appears to be a mannose/glucose-specific legume lectin.

In one embodiment, the pylartin protein comprises a peptide chain designated β (beta), which comprises the sequence AQSLSFSFTKFD (SEQ ID NO:1). Preferably, the β peptide comprises the sequence AQSLSFSFTKFDLD (SEQ ID NO:2). The β peptide has a molecular weight in the range of about 12–20 kD, typically about 13 kD.

In an alternative embodiment, the pylartin protein comprises a peptide chain designated α (alpha), which comprises the sequence VVAVEFD (SEQ ID NO:3). Preferably, the α peptide comprises the sequence TDSYVVAVEFD (SEQ ID NO:4). The α peptide has a molecular weight in the range of about 15–20 kD, typically about 16 kD.

In another embodiment, the protein can include monomeric, dimeric and multimeric proteins, in which one, two, or more than two peptide chains, respectively, occur together as subunits of a single proteinaceous substance, whether of natural or synthetic origin. The subunits of such dimers and multimers may be the same or they may be different. A highly preferred dimer according to the invention is a heterodimer comprising one alpha peptide and one beta peptide (αβ).

The pylartin heterodimers (αβ) may aggregate, presumably by non-covalent interactions, to form a tetramer $(\alpha\beta)_2$ with a mass of about 60 kD. The tetramer appears to be the most common naturally occurring form of the protein, but other multimers, e.g., concatamers of the heterodimer, i.e., $(\alpha\beta)_n$ wherein n is a positive integer larger than 2, may be observable by SDS-PAGE, in mass increments of about 25–30 kD. Accordingly, the invention encompasses all of these configurations. In its mature form as an $\alpha_2\beta_2$ tetramer, the pylartin protein retains biological activity at pH 2–10; multiple freeze-thaw cycles; at 60° C. for ten minutes; and at 4° C. for several months.

Certain molecular features of the pylartin protein indicate that the protein is related to known plant lectins, specifically to lectins derived from legumes. For example, the N-terminal region of the α peptide includes a plant lectin consensus sequence, i.e., residues 5–12 of SEQ ID NO:3. Also, the pylartin protein can occur as a tetramer, a structure common to many lectins.

Other features of the pylartin protein are remarkable and unexpected. For example, the protein of the invention has been obtained, as described below, from the red kidney bean, which is known to produce another lectin (i.e., phytohemagglutinin) in much larger quantities. That a plant would express two such distinctly different lectins is unexpected. It is known that certain plant proteins, such as the aforementioned phytohemagglutinin, have physiological effects in mammals. Nonetheless, it is not expected that any protein of indeterminate function from one taxonomic kingdom would also act as a specific regulator of progenitor cells in another kingdom. Surely such a phenomenon is unexpected and unexplained. In addition, whereas certain eukaryotic proteins are identified as playing a role in developmental control (e.g., Tan-1 for hematopoietic lineages), no comparable role has yet been defined for plant lectins.

As a result of the present invention, numerous utilities become technically feasible. The method of the invention can include contacting the progenitor cells with the pylartin protein in vitro, ex vivo, or in vivo. For example, the pylartin protein finds a utility, inter alia, in that it enables ex vivo maintenance of hematopoietic progenitor cells isolated from either normal or malignant (e.g., leukemic) bone marrow. Accordingly, the protein can be employed in the culture of mononuclear cells derived from a source of such cells, for example, from bone marrow, umbilical cord blood, placental blood, or peripheral blood. Alternatively, the pylartin protein can be used in conjunction with growth factors such as colony stimulating factors (CSFs) (e.g., IL3, GM-CSF, G-CSF, M-CSF), interleukins (e.g., IL1 through IL15) and KL in vitro to selectively induce proliferation and terminal differentiation of mature progenitors while leaving a highly enriched population of primitive progenitors. U.S. Pat. Nos. 5,472,867 and 5,186,931 describe representative methods of using CSFs and interleukins (ILs) to expand progenitor cell populations in the contexts of, respectively, cancer chemotherapy and bone marrow transplants. In a preferred case according to the present invention, the method further includes contacting the progenitor cells with flk2 ligand in an amount sufficient to selectively expand the number of progenitor cells without inducing differentiation thereof.

The pylartin protein also enhances survival of progenitor cells when cultured in vitro. For example, a process of in vitro selection can be used which involves using the protein to preserve progenitor cells in a substantially quiescent state in culture, while using a cytotoxic agent which exhibits selective toxicity for proliferating cells, e.g., to kill cells passing through cell cycle ("cycling cells"). Suitable cytotoxic agents include, for example, compounds such as adriamycin, cyclophosphamide, taxol or other taxane, cisplatin, or 5-fluorouracil. The method is useful to preserve quiescent progenitor cells. The method is effective even when the progenitor cells are substantially free of stromal cells, cells which are considered to normally be necessary for progenitor cell maintenance and proper hematopoietic reconstitution. Pylartin improves the ability to functionally select stem cells either alone or with other factors. Such functional selection methods, include the method reported by Berardi et al. (1995) where selection is made using a combination of KL and IL3 with 5-FU.

Ex vivo purging protocols can be used to selectively eliminate neoplastic cells by targeting the elimination of actively cycling cells. By preserving progenitor cells in a quiescent state, the protein of the invention preserves normal progenitor cells, while the cycling cells are killed. Once the progenitors cells have been purged of malignant cycling cells, they can be returned to the patient, and permitted to resume normal proliferation and differentiation. In one especially useful scenario, the pylartin protein allows for functional selection of normal progenitor cells from a leukemic bone marrow. Such functional selection and purification of primitive stem cells can also be used to enable allogeneic transplant procedures.

The pylartin protein also enables ex vivo manipulation of hematopoietic progenitor cells for use in gene therapy by maintaining cells in liquid culture. For example, by preserving hematopoietic progenitor cells in culture for more than two weeks, the protein enables increased targeting efficiency by viral vectors that enter non-replicating cells (e.g., vectors such as adeno-associated viruses), and provides longer periods for the evaluation of the resultant cell populations to determine efficiency of transfection. Thus, in another embodiment, the method can be used in conjunction with methods of transfecting an exogenous DNA sequence into somatic cells. The method can then include transfecting progenitor cells selectively preserved by the pylartin protein.

The invention also has utility in conjunction with therapies, e.g., cancer therapies, which employ irradiation. Specifically, because the pylartin protein maintains progenitor cells in a quiescent state, administration of the pylartin protein to a mammalian subject in vivo allows the use of increased levels of total body irradiation to eliminate neoplastic cells, while leaving quiescent cells relatively unaffected. The protein can be employed in conjunction with other cytoprotective substances such as IL-1 to obtain an enhanced or complementary effect.

Thus, the method can involve treating a mammalian subject in need of hematopoietic therapy. For example, a tissue sample including hematopoietic progenitor cells can be obtained from the subject. Then the tissue sample can be cultured ex vivo in the presence of the pylartin protein to preserve the progenitors, while allowing cycling cells to proliferate, differentiate and die. The cultured cells become highly enriched in the primitive progenitor cells. Meanwhile, the mammal can be subjected to conditions sufficient to effect myeloablation, e.g., bone marrow irradiation, whole body irradiation, or chemically-induced myeloablation. Finally, the progenitor-enriched cultured cells can be administered to the mammal following the myeloablation to reconstitute the hematopoietic system of the mammal While described here as an autologous procedure, the skilled practitioner will recognize that the method can be readily adapted to transplant of progenitor-enriched cells from one individual to another.

The pylartin protein also improves hematopoietic competence in a mammal, i.e., the mammal's ability to generate functional mature blood elements. For example, a tissue sample comprising hematopoietic progenitor cells can be cultured in a growth medium containing the pylartin protein in an amount sufficient to preserve the progenitor cells and to provide cultured cells enriched in the progenitor cells. Then, the enriched cultured cells are transfused to the mammal to provide progenitor cells for generating blood cellular components in the mammal This method can further comprise ablating hematopoietic tissues in the mammal prior to the transfusing. In addition, the method can use a tissue sample comprising peripheral blood, umbilical cord blood, placental blood, or bone marrow. Preferably, the tissue sample is autologous to the mammal. The tissue sample can also be at least substantially free of stromal cells.

The invention further includes a composition for maintaining viability of progenitor cells ex vivo or in vitro. The composition comprises a culture medium suitable for growth and maintenance of mammalian cells in culture, along with an amount of the pylartin protein sufficient to preserve progenitor cells as described herein. Virtually any cell or tissue culture medium can be modified for the preservation of progenitors in this way. Ready-to-use receptacles, e.g., blood bags, microtiter plates, and tissue culture flasks, and the like, can also be provided with the pylartin protein (with or without culture medium or other active components) to promote culture of progenitor cells.

Also, the invention includes a method for preserving progenitor cells in a mammal in vivo. In this approach, the method comprises administering to the mammal the pylartin protein in an amount sufficient to preserve progenitor cells of the mammal in a substantially non-proliferative state. The mammal is then exposed to myeloablative conditions sufficient to effect ablation of proliferating myeloid cells but sparing non-proliferating progenitor cells. Following the ablative treatment, proliferation or differentiation of the preserved progenitor cells is reestablished, usually by administering to the mammal a cytokine in an amount sufficient to improve the viability of the progenitor cells. Preferred viability-improving cytokines include, for example, IL1, IL3, IL6, IL11, KL, or a combination thereof. More preferably, the reestablishing comprises administering to the mammal a proliferation-stimulating amount of the flk2 ligand. According to this method, the pylartin protein can be used to enhance autologous bone marrow transplantation techniques in which lethal doses of radiation and/or chemotherapy are followed by reinfusion of stored marrow.

An effective amount of pylartin protein can be administered to a mammal by any convenient approach, such as parenteral routes, e.g., intravenous injection, or preferably by enteral routes. Oral administration routes are expected to be useful since lectins typically resist oral/gastric degradation, and can exhibit substantial bioavailability by this approach. The skilled artisan recognizes the utility and limitations of various methods of administration and can adjust dosage (posology) accordingly.

Other therapeutic utilities also present themselves to the skilled practitioner as being enabled by the invention. Such other utilities include, for example, expanding progenitor cell populations ex vivo to increase chances of engraftation, improving conditions for transporting and storing progenitor cells, and removing a fundamental barrier to enable gene therapy to treat and cure a broad range of life-threatening hematologic diseases such as sickle cell anemia and thalassemia.

The protein of the invention can also be used as a specific probe for the identification or localization of progenitor cells. Since the protein binds specifically to primitive progenitor cells, a composition including the protein linked to a detectable moiety such as a fluorescent marker can be used to specifically label and identify progenitor cells. Thus, cell sorting to isolate progenitor cells can be performed, as can histologic localization of progenitor cells in tissues. The skilled artisan can select the type or marker moiety to be employed according to the task to be performed, since numerous methods of labeling proteins are known in the art.

The following examples are provided to assist in a further understanding of the invention. The particular materials and conditions employed are intended to be further illustrative of the invention and are not limiting upon the reasonable scope thereof.

EXAMPLE 1

Isolation of the Pylartin Protein from Kidney Beans and Hyacinth Beans

Two hundred fifty grams (250 g) of kidney beans obtained from a commercial source (Stokes Seed Company, Buffalo, N.Y. or W. Atlee Burpee & Co, Warminister, Pa.) was pulverized in a coffee grinder. (This method can also be used to isolate material from hyacinth beans or other beans containing an active substance in accordance with the invention.) The bean powder was added to 1 L of an alkaline lectin binding buffer (LBB; e.g., 50 mM Tris/HCl, pH 7.0, containing metal cations: 1 mM each of $MgCl_2$ and $CaCl_2$) and incubated with constant mixing overnight at 4° C. The particulate matter was pelleted by centrifugation at 10,000× g for 20 min and the supernatant was retained.

The protein binds specifically to mannose, enabling a single step purification of the protein. To remove contaminants that could interfere with mannose-agarose affinity chromatography, the bean supernatant was exposed to ammonium sulfate precipitation using 60% (0.6 g/mL). The precipitate was resuspended, and dialyzed overnight at 4° C. against LBB, to provide the starting material for affinity chromatography. The dialyzed ammonium sulfate fraction was incubated with mannose covalently coupled to Sepharose 4B (Sigma Chemical Co., St. Louis, Mo.) overnight on a rocker at 4° C. The gel was then washed extensively with LBB and pelleted by gravity sedimentation. Lectins were eluted with 250 mM methyl α-D-methylpyranoside (Sigma Chemical Co., St. Louis, Mo.) in LBB for two days on a rocker at 4° C., pelleted by density sedimentation, and the lectin-containing supernatant aspirated. The supernatant containing the pylartin protein was dialyzed overnight against LBB to remove sugar, and the resulting dialysate was sterile filtered, and stored at −20° C.

FIG. 1 shows SDS-PAGE analysis of purified pylartin protein isolated from hyacinth beans, and purified by mannose-agarose. Pylartin samples and molecular markers (Integrated Separation Systems, Natwick, Mass.) were analyzed under reducing conditions on a 10–27% gradient polyacrylamide gels (Integrated Separation Systems, Natwick, Mass.) and visualized by Coomassie Brilliant Blue staining (Sigma Chemical Co., St. Louis, Mo.). Molecular weights are indicated on left side of the gel; alpha and beta subunits are indicated for each on the right side of each gel and numbers indicate isoforms of subunits. Four isoforms of the alpha subunit and one of the beta subunit of pylartin were detected in the hyacinth bean.

EXAMPLE 2 flk2 Receptor 3T3 Assay Specifically Quantitates Biological Activity of the Pylartin Protein The pylartin protein interacts with the mammalian flk2 tyrosine kinase receptor. A specific and quantitative biological assay using NIH 3T3 fibroblasts transfected either with a chimeric receptor consisting of the extracellular portion of the murine flk2 receptor combined with the intracellular portion of the human Fms receptor (Lemischka et al., unpublished) or with the full length human receptor (Small et al. 1994) can be used to evaluate lectin biological activity during purification. Serial two-fold dilutions of lectin samples across rows of a 96 well plate allowed for greater than a thousand-fold range to access flk2 3T3 biological activity. The assay requires either the murine or human flk2/flt3 ligand (FL) (Lyman et al. 1993; Hannum et al. 1994) or the pylartin protein to rescue flk2-transfected cells from death.

Specifically, remove 3T3 cells from stock culture plates by washing cells cultured in tissue culture plates (Becton Dickinson Labware, Lincoln Park, N.J.) twice in Hank's buffered saline (HBSS; Gibco Laboratories, Grand Island, N.Y.) followed by addition of non-enzymatic cell dissociation buffer (Gibco) for 15 minutes at room temperature, and subsequently wash cells in medium. Culture flk2 3T3 cells at a final concentration of 3,000 cells per well in a volume of 100 µL of serum-defined medium containing 10% AIMV (Gibco) and 90% Dulbecco's modification of Eagle's medium (DMEM; Gibco) in 96 well plates. Under these assay conditions, cells die after two to four days of culture in a humidified incubator at 37° C. and 5% $CO_2$ unless exogenously added ligand rescues cells from death. Each 96 well plate contains calf serum, which stimulates all 3T3 cells, as a positive control and medium only as a negative control. Full-length Fms-transfected 3T3 cells (biological response shown in Tessler et al. 1994) serve as receptor-transfected control target cells, and parent 3T3 cells serve as untransfected control cells. Proliferation and cell survival is quantitated by addition of XTT (Diagnostic Chemicals Ltd, Charlottetown, Prince Edward Island, Canada), a tetraformazan salt cleaved by actively respiring cells (Mosmann 1983), and quantitated spectrophotometrically using a Vmax kinetic plate reader (Molecular Devices Corp., Mountain View, Calif.), and recorded as either relative activity (units/mL) or as specific activity (units/mg). One unit of biological activity is defined as the reciprocal dilution at which half-maximal stimulation of cells is detected. FIGS. 2A–2D show that pylartin isolated from red kidney beans specifically stimulates flk2 3T3 cells in an IL1-dependent manner. Pylartin biological activity was tested over a 1,000-fold range on flk2/Fms 3T3 cells (FIGS. 2A and 2B) and parent untransfected 3T3 cells (FIGS. 2C and 2D) in the absence (FIGS. 2A and 2C) and presence (FIGS. 2B and 2D) of 10 ng/mL human recombinant interleukin 1-alpha (IL1α) (BioSource International, Camarillo, Calif.) and quantitated by XTT. The pylartin protein stimulated proliferation of flk2/Fms 3T3 cells only in the presence of IL1, and did not stimulate proliferation of untransfected 3T3 cells regardless of whether IL1 was present or not.

Examples 3–10, below, show that the protein of the invention preserves progenitors cells in vitro. Pylartin isolated from red kidney beans and hyacinth beans specifically preserves progenitors derived from murine fetal liver cells and human cord blood cells in liquid culture.

EXAMPLE 3

The Pylartin Protein Preserves Human and Murine Hematopoietic Progenitor Cells In Vitro Hematopoietic progenitor cells range in frequency from about 1:10,000 to about 1:100,000 of mononuclear cells in human bone marrow, umbilical cord blood, and under certain conditions, peripheral blood. Enrichment of progenitor cells for in vitro culture involves isolating mononuclear cells from a sample of whole blood or blood marrow by density separation. Specifically, the sample is gently layered over Ficoll-Paque Plus (Pharmacia Biotech, Piscataway, N.J.) in a 50 mL conical tube (Becton Dickinson, Franklin Lakes, N.J.) and the samples are processed according to the manufacturer's directions.

Enrichment of stem cells greater than a hundred-fold from mononuclear cell preparations can be achieved using antibody-labeled magnetic bead technology. Two commercial methods (DYNABEADS, available from Dynal Corp., Lake Success, N.Y., and MINIMACS multiparameter sorting, Miltenyi Biotec, Auburn, Calif.), rely on positive selection of $CD34^+$ cells. Another method (STEMSEP $CD34^+/CD38^-$, available from Stem Cell Technologies, Inc., Vancouver, BC) isolates stem cells by negative selection (glycophorin A, CD14, CD3, CD16, CD2, CD66b, CD56, CD36, CD24, CD45RA, CD19, CD38), resulting in cells with the surface phenotype of $CD34^+$, $CD36^-$, $CD38^-$, $CD45RA^-$.

The pylartin protein is used to preserve the isolated progenitor cells, either within a population of mononuclear cells or in enriched $CD34^+$ cells, in liquid culture containing serum-defined medium (AIMV-V from Gibco, Grand Island, N.Y.; BIT9500 from Stem Cell Technologies, Vancouver, BC; or X-VIVO 10 from BioWhittaker, Walkersville, Md.) in an incubator maintained at 37° C. and flushed with 5% $CO_2$, for two to four weeks. The resultant cell population is characterized by flow cytometry, and hematopoietic colony assays are performed to enumerate and evaluate the functional status of the progenitor cells.

Human hematopoietic stem cells express the cell surface antigen phenotypic profile of $CD34^{++}$ $CD38^-$ $Thy^+$, but do not express antigens for mature blood cell lineages (CD3, CD19, etc.)(Peltzer et al. 1996). Specifically, cells are incubated with fluorescent-labeled antibodies (e.g., Coulter Corp., Hialeah, Fla.) following manufacturer's directions and are evaluated for marker expression by flow cytometry (e.g., Epics Elite, Coulter Corp.).

Hematopoietic colony assays indirectly assess the frequency and primitive status of progenitors in a population of cells. Cells are cultured in semi-solid methylcellulose containing growth factors for optimal stimulation of cell proliferation and differentiation (Stem Cell Technologies, Vancouver, BC).

EXAMPLE 4

Pylartin Preserves Murine Fetal Liver CD34$^+$ Cells in Culture

Figure 3:
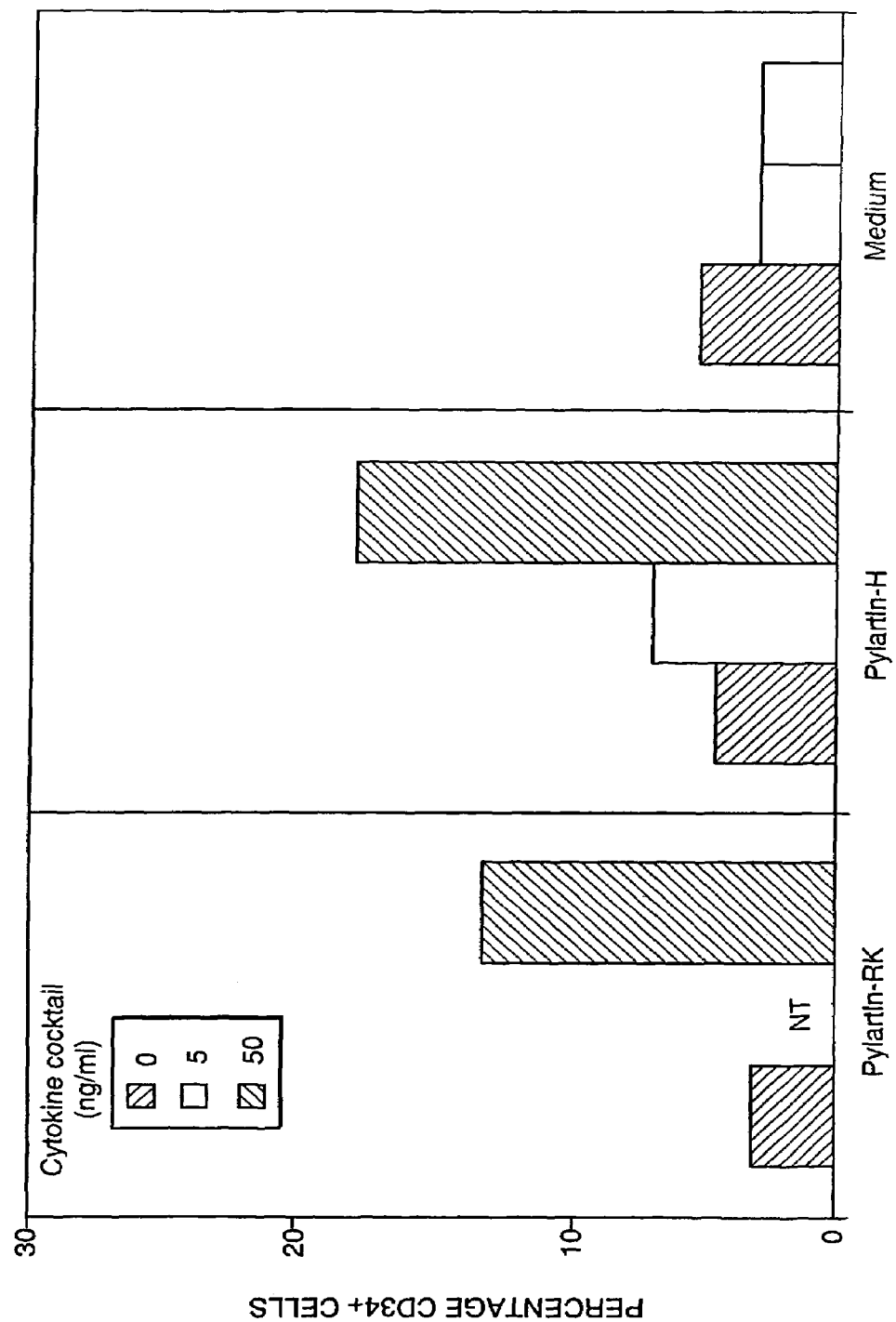
FIG. 3 is a series of histograms comparing the protein of the invention, obtained from red kidney beans, and from hyacinth beans, against culture medium control, showing that the protein of the invention specifically preserves murine CD34$^+$ cells in liquid culture, with and without a cocktail of cytokines including mIL1, mIL3, and mKL.

FIG. 3 shows that purified pylartin isolated from red kidney beans (Pylartin-RK) and hyacinth beans (Pylartin-H), either alone or together with increasing concentrations of a cytokine cocktail (mIL1, mIL3, mKL), preserves murine fetal liver CD34$^+$ cells for six days in liquid culture medium containing 10% calf serum in DMEM. After fifteen days the cultures were harvested and cells replated in a methylcellulose colony assay to assess frequency of functional progenitors. NT indicates not tested. Mononuclear cells cultured in the presence or absence of pylartin with either no exogenous cytokines or a cocktail of early-acting recombinant murine cytokines (mIL1, mIL3, mKL) (BioSource International, Camarillo, Calif.) all at either 5 ng/mL or 50 ng/mL. Flow cytometric analysis of remaining viable cells shows that the proportion of CD34$^+$ cells in culture wells containing pylartin increases in a dose-dependent manner of early acting cytokine cocktail is present but not in medium control.

EXAMPLE 5

Pylartin Preserves Murine Hematopoietic Progenitors in Culture

Figure 4:
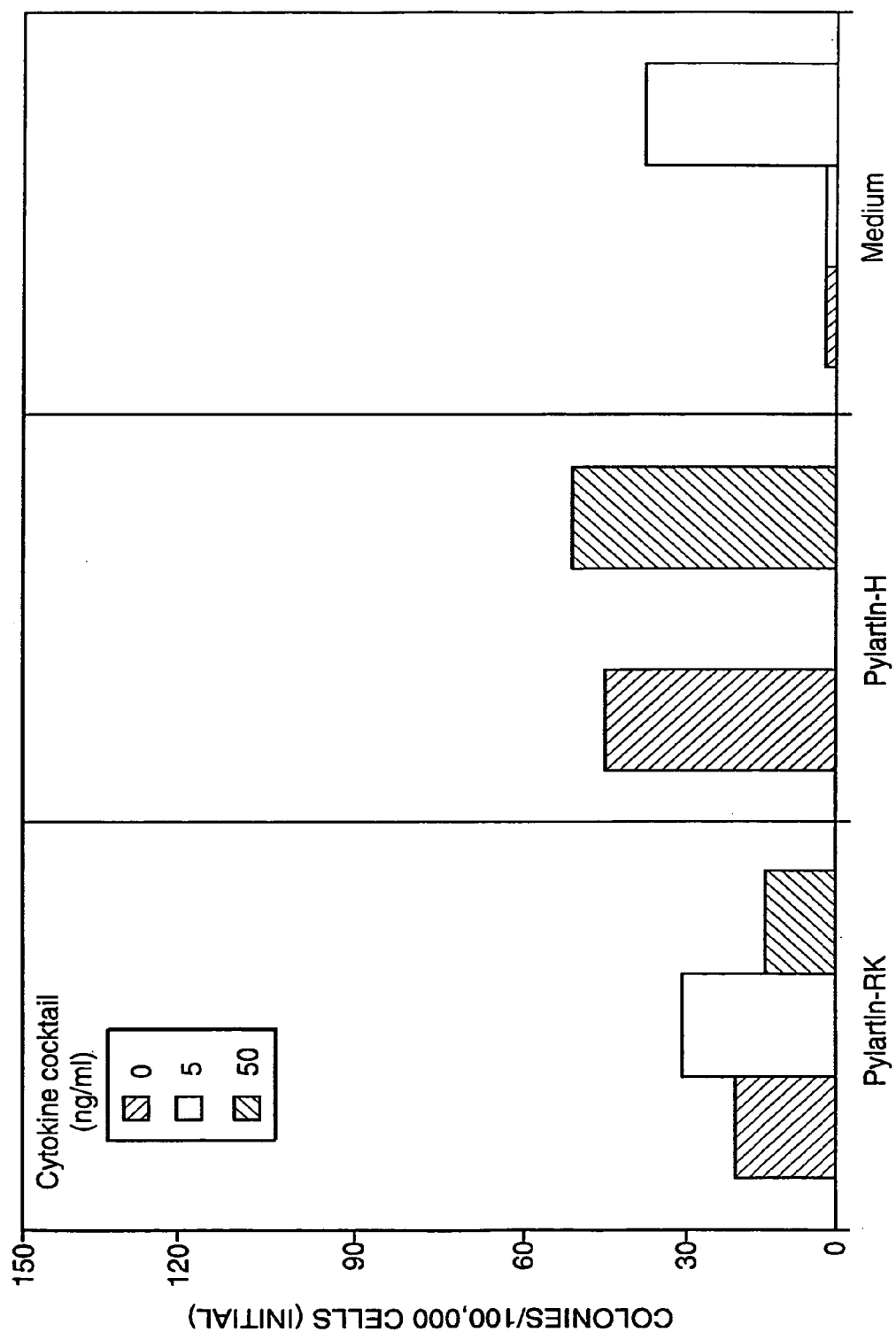
FIG. 4 is a series of histograms comparing the protein of the invention, obtained from red kidney beans or hyacinth beans, against culture medium control, showing that the protein of the invention specifically preserves murine progenitor cells in a methylcellulose colony assay, with and without a cocktail of cytokines including mIL1, mIL3, and mKL.

The pylartin protein, either alone or in combination with either IL1 or FL, preserves functional hematopoietic progenitors for at least two weeks in culture. Specifically, FIG. 4 shows the preservative effect of purified pylartin on murine hematopoietic progenitors cultured fifteen days in liquid culture medium containing 10% calf serum in DMEM. Evaluation of functional progenitors was tested by harvested cells in liquid culture and replated in methylcellulose colony assays (Stem Cell Technologies, Vancouver, British Columbia) according to the manufacturer's instructions. Colonies derived from individual progenitors were scored after two weeks; results were normalized for frequency of colonies per 100,000 cells initial seeded. Each of the pylartin samples preserved progenitors in the absence of the exogenous cytokine cocktail (left bars each group); variable differences were observed for cytokine cocktail-containing pylartin samples.

EXAMPLE 6

Figure 5:
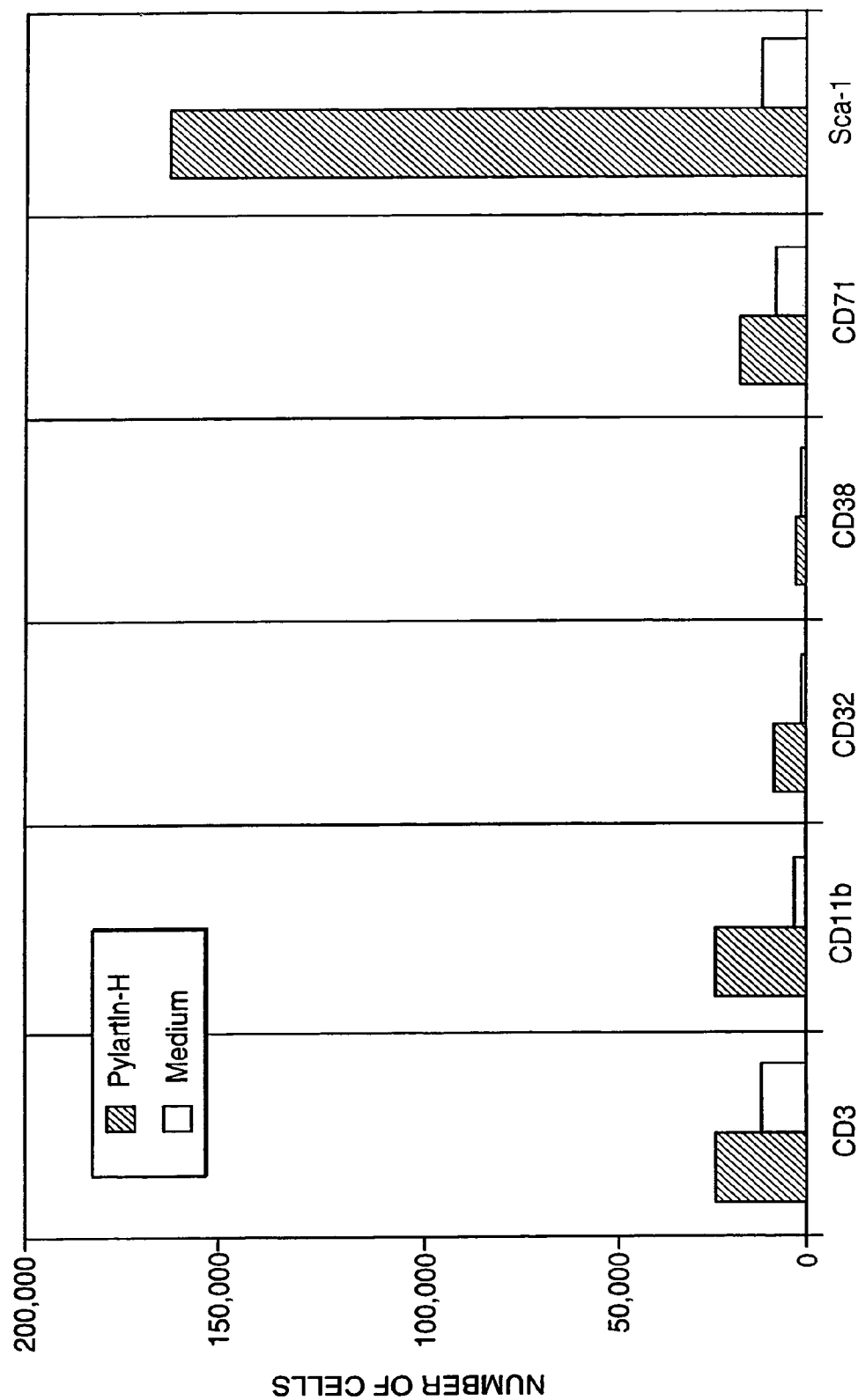
FIG. 5 is a series of histograms showing the results of flow cytometric study of six different cell surface markers showing that the protein of the invention specifically preserves primitive murine progenitors.

Flow Cytometric Analysis of Cell Surface Markers on Cells Cultured with Pylartin Protein The type of cells generated in methylcellulose colony assays in cultures containing 50 ng/mL of the cytokine cocktail (FIG. 4) was determined by flow cytometry. These data are summarized in FIG. 5. Sca$^+$ cells were greatly increased in pylartin-containing cultures, other cell surface markers were not particularly affected. The Sca antigen is expressed on murine stem cells and other mature cells including T cells. In this experiment, T cells (CD3) were not increased. FIG. 5 shows a flow cytometric analysis of the cell surface phenotype of cells harvested from cells cultured in 50 ng/mL of early-acting recombinant murine cytokines (mIL1, mIL3, mKL) (BioSource International, Camarillo, Calif.), in the presence and absence of pylartin samples, prior to colony assay (far right bars from FIG. 4). Pylartin-RK generated 14.5-fold more Sca-1 cells than medium control. Sca-1, or Ly6, is an antigen associated with primitive murine progenitors and also mature blood cells including T cells, etc. (Spangrude et al. 1991). No differences were observed in the numbers of T cells (CD3), dendritic cells (CD11b), or cells expressing the Fc-gamma receptor (e.g., granulocytes and monocytes), CD38, or the transferrin receptor (CD71) (antibodies obtained from Pharmigen, Calif.).

EXAMPLE 7

The Pylartin Protein Preserves Human CD34$^+$ Cells in Culture

Figure 6A:
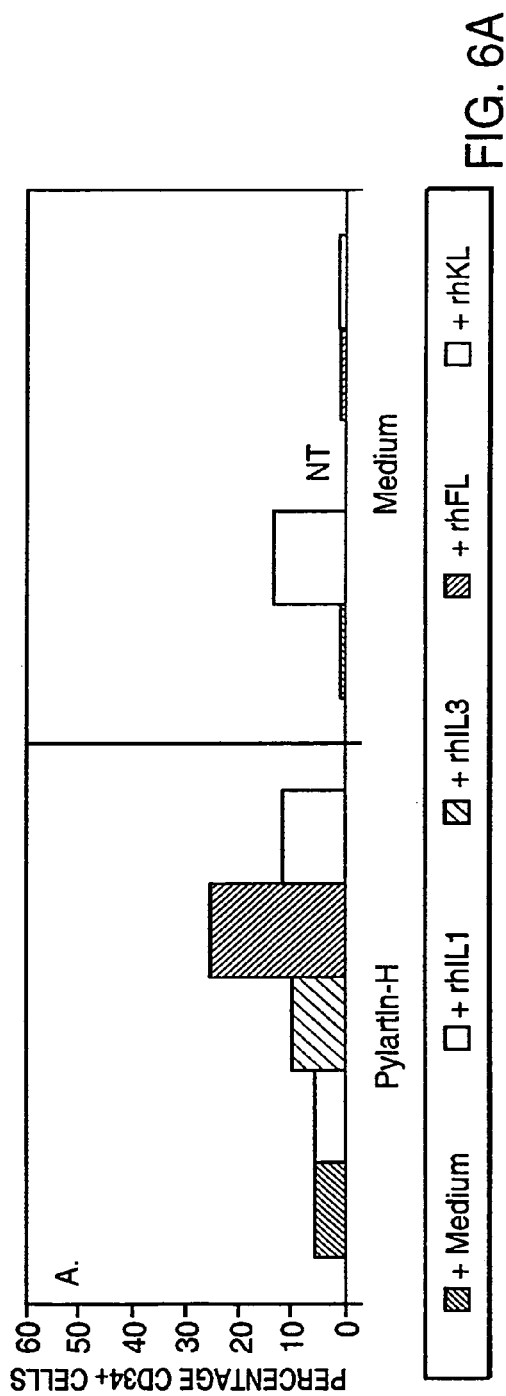
FIG. 6A is a set of histograms comparing the protein of the invention against culture medium control, showing that the protein of the invention specifically preserves CD34$^+$ human cord blood cells in liquid culture for six days.
Figure 6B:
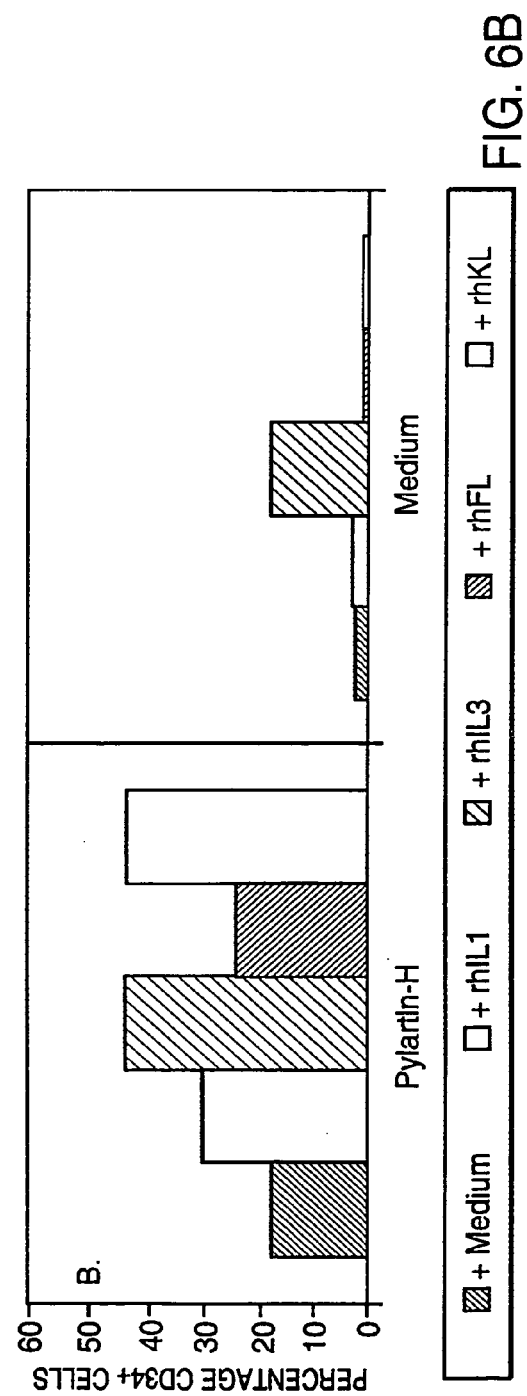
FIG. 6B is a complementary set of histograms showing that the protein of the invention specifically preserves CD34$^+$ human cord blood cells in liquid culture for 17 days.

Pylartin also preserves human primitive progenitors. FIGS. 6A and 6B show that pylartin, either alone or in combination with early-acting human cytokines (rhIL1-α, rhIL3, rhFL, rhKL), specifically preserves CD34$^+$ human cord blood cells for up to two weeks. The purified pylartin isolated from hyacinth beans (Pylartin-H) specifically preserves human cord blood cells that express the CD34 antigen for seventeen days (FIG. 6A) and six days (FIG. 6B) in liquid culture containing a serum-defined medium (BIT9500, Stem Cell Technologies, Vancouver, British Columbia). Pylartin is effective to preserve CD34$^+$ cells either with or without added exogenous cytokines.

EXAMPLE 8

The Pylartin Protein Preserves Human Progenitors in Liquid Culture

Figure 7:
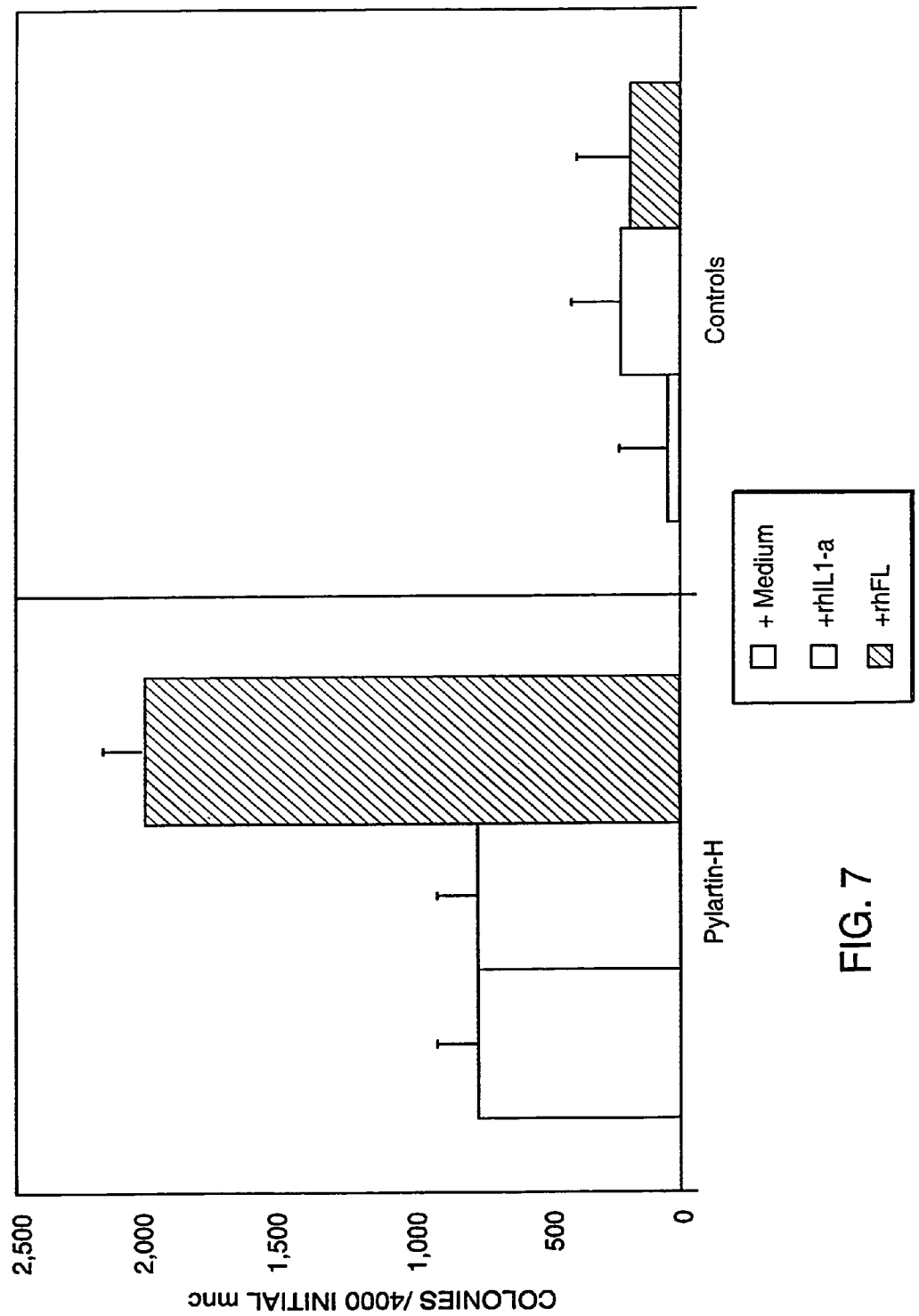
FIG. 7 is a set of two histograms comparing the protein of the invention against a control, illustrating that the pylartin protein, either alone or in combination with IL1-a or FL preserves or increases the number of human progenitor cells in a methylcellulose colony assay.

The pylartin protein, either alone or in combination with either IL1 or FL, preserves functional progenitors for at least two weeks in liquid culture. FIG. 7 shows in this is experiment the combination of pylartin and FL actually increases the number of progenitors in liquid culture under selected assay conditions. The number of colonies derived from functional progenitors is several times greater where pylartin is present (left panel) than in medium control (right panel), with or without exogenous IL1 or FL.

The nature of hematopoietic progenitors preserved by pylartin in liquid culture changes over time. Cord blood mononuclear cells (mnc) were cultured in X-VIVO 10 at a concentration of 800,000 cells in 4 mL for 6, 15, and 21 days with either pylartin, FL, pylartin +FL, or medium control. Functional progenitors were assessed by replating cells in methylcellulose colony assays and scoring colonies after an additional 16 days. Four types of colonies were recorded: "Blast" refers to small, dispersed colonies consisting of undifferentiated cells which may represent very primitive stem cells; "Mix" refers to colonies consisting of differentiated myeloid and erythroid cells formed by multilineage progenitors; "Myeloid" refers to colonies consisting exclusively of differentiated myeloid cells; "Erythroid" refers to colonies consisting exclusively of differentiated erythroblasts or normoblasts formed by primitive progenitors called "BFU-E" (burst-forming unit erythroid).

Colonies formed in all liquid culture wells after six days of culture (FIG. 8A) The solid line in FIG. 8A indicates too many colonies to accurately score, which in this experiment was greater than 1,500 colonies per 800,000 mnc.

After 15 days of culture pylartin but not FL preserves relatively mature progenitors of myeloid or erythroid lineages (FIG. 8B). "Blast"-like cells and myeloid-committed progenitors appear in methylcellulose colony assay plates from cord blood mononuclear cells preserved in liquid culture for 21 days (FIG. 8C). The relatively high frequencies of progenitors cultured for 15 and 21 days indicate not only preservation of progenitors but also an increase (self-renewal) of primitive progenitors.

EXAMPLE 9

Pylartin Preserves Progenitor Cells in Culture in a Dose-Responsive Manner

Figure 9B:
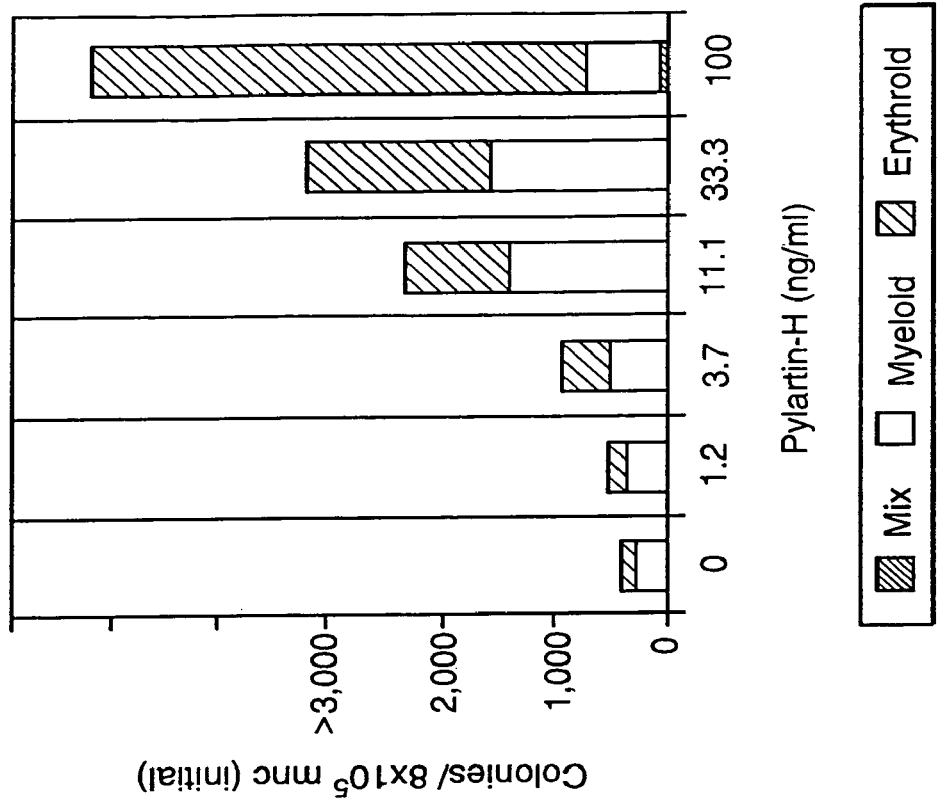
FIGS. 9A and 9B are a set of histograms showing that the protein of the invention preserves hematopoietic progenitors in a dose-responsive manner.
Figure 9A:
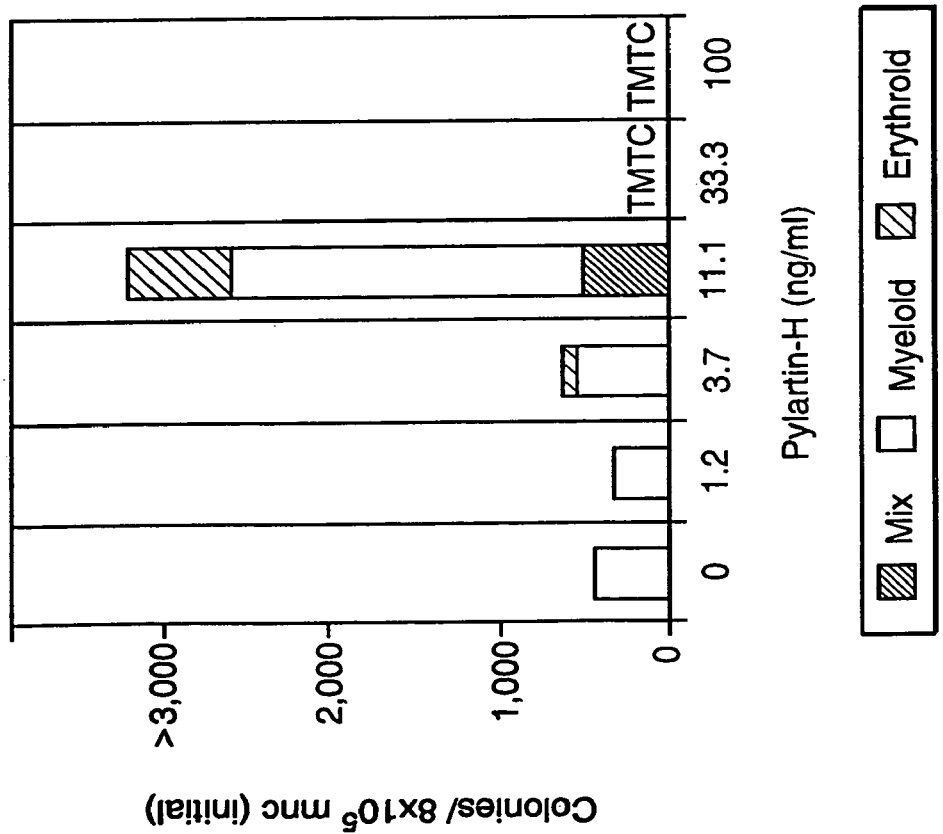

Pylartin acts in a dose-responsive manner to preserve human cord blood progenitors. FIGS. 9A–9B show results from culturing cord blood mononuclear samples from two donors (FIGS. 9A and 9B, respectively) using the method described in Example 8. In this case, cultures were maintained for 12 days over a 100-fold concentration range of pylartin. Although the response differed between the two donors—both in composition of colony types and progenitor frequency—the specific activity of DLL, at 20,000 units/mg, is approximately the same in each case. TMTC indicates too many colonies to count.

EXAMPLE 10

Figure 10:
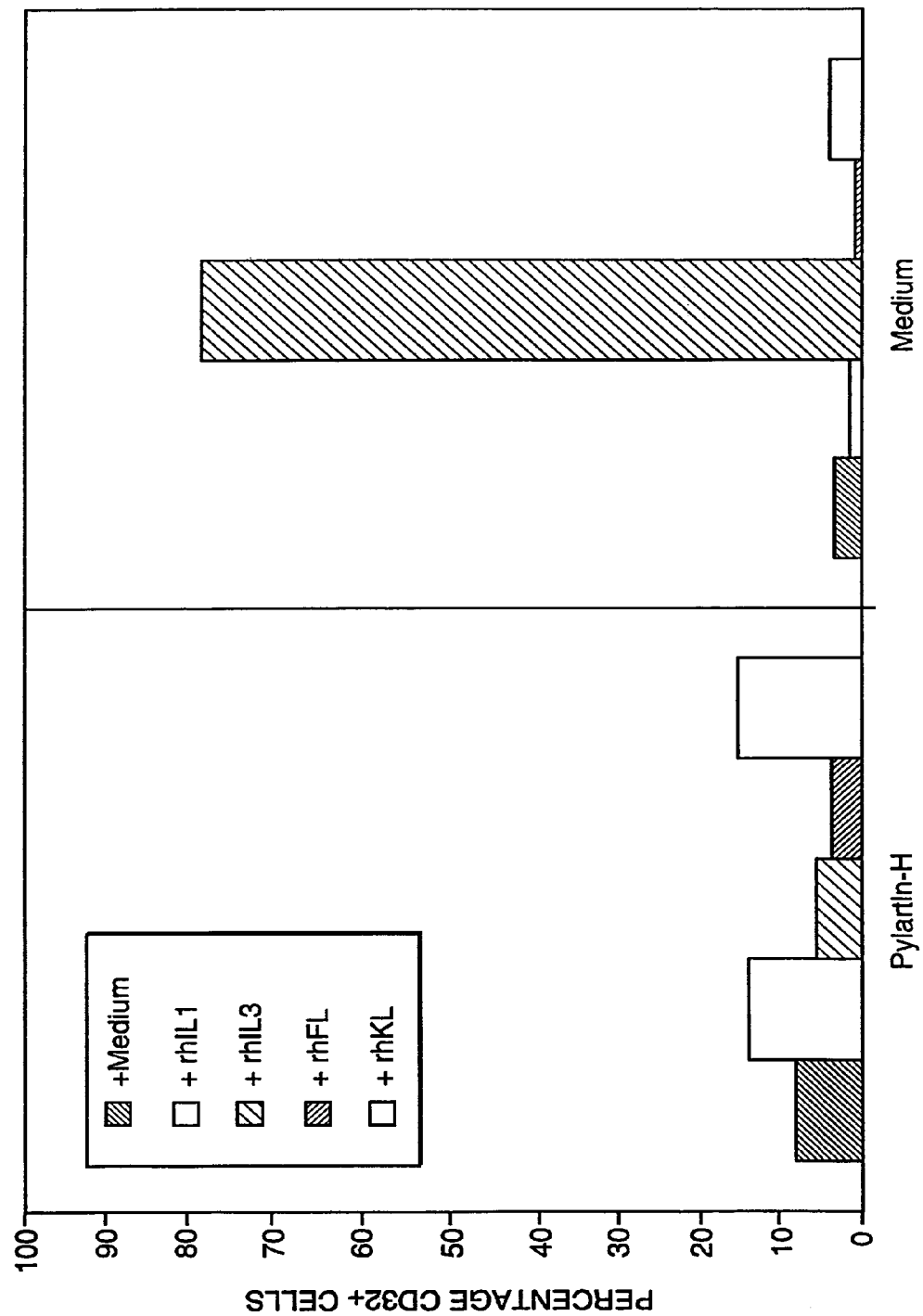
FIG. 10 is a pair of histograms, comparing the protein of the invention against medium control, illustrating that the pylartin protein preserves progenitors by preventing IL3-induced differentiation.

Pylartin Preserves Progenitors in Culture by Preventing Differentiation into Mature Blood Cells FIG. 10 shows that pylartin, obtained in this case from hyacinth beans, prevents IL3-induced production of cells expressing the Fc-gamma receptor after six days in liquid culture. IL3-containing cultures contained approximately 80% $CD32^+$ cells, while pylartin-containing cultures contained <10% $CD32^+$ cells. Cells that express FcγII and FCγIII receptors in mice include natural killer cells, monocytes, macrophages, granulocytes, mast cells, as well as fetal thymocytes (Unkeless 1979).

The data presented in the above Examples demonstrate that pylartin preserves primitive hematopoietic progenitors, either alone or in combination with other cytokines, and prevents IL3-induced differentiation in liquid culture. Indeed, the protein by itself is more effective in preserving progenitors than FL even when the latter is supplemented with stromal cells. While no data have yet been obtained to test whether the peptide and stromal cells are cultured together, applicants believe that a potentiation of the preservative affect of the peptide would be maintained. Nonetheless, it is apparent that the protein of the invention is effective in preserving primitive hematopoietic progenitors in cell culture. This implies that the protein is effective for use in clinical methods involving explanation of progenitors, culture and preservation of the progenitors ex vivo, and subsequent reimplantation (or transplantation) of the preserved progenitors.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

The following publications, mentioned in the foregoing specification, are incorporated herein by reference for all that they disclose:

Baronedes, S H, "Bifunctional properties of lectins: Lectins redefined," Trends Biochem. Sci. 13:480–482 (1988).

Berardi, A C et al., "Functional isolation and characterization of human hematopoietic stem cells," Science, 267: 104–108 (1995).

Dwek, R A, "Glycobiology: More function for oligosaccharides," Science 269: 1234–1235 (1995).

Gabius, H-J, "Non-carbohydrate binding partners/domains of animal lectins," Int. J. Biochem. 26:469 (1994a).

Gabius, H-J, "Lectinology meets mythology: Oncological future for the mistletoe lectin?," Trends in Glycosci and Glycotech 6:229 (1994b).

Gowda, L R, H S Savithri, and D R Rao, "The complete primary structure of a unique mannose/glucose-specific lectin from field bean (Dolichos lab lab)," J. Biol. Chem. 269:18789–18793 (1994).

Hannum, C O et al., "Ligand for Flt3/flk2 receptor tyrosine kinase regulates growth of hematopoietic stem cells and is encoded by variant RNAs," Nature 368:643 (1994).

Lyman, S D et al., "Molecular cloning of a ligand for the Flt3/flk2 tyrosine kinase receptor: a proliferative assay for primitive hematopoietic cells," Cell 75:1157 (1993).

Mosmann, T, "Rapid colorimetric assay for cellular growth and survival: Application to proliferation and cytotoxicity assays," J. Immunol. Methods 65:55–63 (1983).

Ogawa, M, "Differentiation and proliferation of hematopoietic stem cells," Blood 87:2855 (1993).

Peltzer, A L et al., "Self-renewal of primitive human hematopoietic cells (long-term-culture-initiating cells) in vitro and their expansion in defined medium," Proc. Natl. Acad. Sci. (USA), 93:1470–1474 (1996).

Shah, A J et al., "flt3 Ligand induces proliferation of quiescent human bone marrow $CD34^+CD38^-$ cells and maintains progenitor cells in vitro," Blood, 87:3563–3570 (1996).

Sharon, N, and H Lis, "Lectins as cell recognition molecules," Science, 246:227–234 (1989).

Small, D. M Levenstein, E Kim, C Carow, S Amim, P Rockwell, L Witte, C Burrow, M Ratajczak, A M Gewirtz, and C Civin, "STK-1, the human homolog of flk-2/flt3, is selectively expressed in $CD34^+$ human bone marrow cells and is involved in the proliferation of early progenitor/stem cells," Proc. Natl. Acad. Sci. USA, 91:459–463 (1994).

Spangrude, G J, et al., "Purification and characterization of mouse hematopoietic stem cells," Science 241:58–62 (1991).

Tessler, S, P Rockwell, D Hicklin, T Cohen, B-Z Levi, L Witte I R Lemischka, and G Neufeld, "Heparin modulates the interaction of VEGF165 with soluble and cell associated flk-1 receptors," J. Biol. Chem. 269:12456–12461 (1994).

Turhan A G, et al., "Clonal hematopoiesis demonstrated by x-linked DNA polymorphisms after allogeneic bone marrow transplantation," N. Engl. J. Medicine, 320:1655–1661 (1989).

Unkeless, J C, "Characterization of a monclonal antibody directed against mouse macrophage and lymphocyte Fc receptors," *J. Exp. Med* 150:580–596 (1979).

Young, J C, A Varma, D DiGiusto, and M Backer, "Retention of quiescent hematopoietic cells with high proliferative potential during ex vivo stem cell culture," *Blood* 87:545–556 (1996).

Zipori, D, "The renewal and differentiation of hemopoietic stem cells," *FASEB J.* 6:2691–2697 (1992).

---

What is claimed is:

1. A pharmaceutical composition comprising:
   (a) a carrier; and
   (b) a mannose-binding protein which is a lectin comprising a heterodimer of a first polypeptide and a second polypeptide, wherein the first polypeptide has a molecular weight of about 12–20 kDa, and wherein the second polypeptide has a molecular weight of about 15–20 kDa;
   wherein the lectin can be obtained from a legume selected from the group consisting of *Phaseolus vulgaris, Dolichos lab lab,* and *Vigna senensis.*

2. The pharmaceutical composition of claim 1, wherein the lectin is obtained from an extract of a plant selected from the group consisting of *Phaseolus vulgaris, Dolichos lab lab,* and *Vigna senensis.*

3. The pharmaceutical composition of claim 1, wherein the lectin is capable of binding the flk2/flt3 receptor.

4. The pharmaceutical composition of claim 1, wherein the lectin is capable of stimulating proliferation of NIH 3T3 fibroblasts expressing the flk2/flt3 receptor in an IL1-dependent manner.

5. The pharmaceutical composition of claim 1, wherein the lectin is capable of preserving progenitor cells.

6. The pharmaceutical composition of claim 5, wherein the progenitor cells are at least unipotent progenitor cells.

7. The pharmaceutical composition of claim 5, wherein the progenitor cells are pluripotent progenitor cells.

8. The pharmaceutical composition of claim 5, wherein the progenitor cells are totipotent progenitor cells.

9. The pharmaceutical composition of claim 5, wherein the progenitor cells comprise hematopoietic progenitor cells.

10. The pharmaceutical composition of claim 5, wherein the progenitor cells comprise human CD34+ cells.

11. The pharmaceutical composition of claim 5, wherein the progenitor cells comprise murine fetal liver CD34+ cells.

12. The pharmaceutical composition of claim 9, wherein the progenitor cells express the CD34 antigen.

13. The pharmaceutical composition of claim 9, wherein the progenitor cells express the flk2/flt3 receptor.

14. The pharmaceutical composition of claim 1, wherein the lectin is capable of preserving cells modified to express the flk2/flt3 receptor on their surface.

15. The pharmaceutical composition of claim 5, wherein the progenitor cells are selected from the group consisting of nerve, muscle, skin, gut, bone, kidney, liver, pancreas or thymus progenitor cells.

* * * * *

UNITED STATES PATENT AND TRADEMARK OFFICE
CERTIFICATE OF CORRECTION

PATENT NO. : 7,112,653 B2 Page 1 of 1
APPLICATION NO. : 10/737180
DATED : September 26, 2006
INVENTOR(S) : Jeffrey G. Moore It is certified that error appears in the above-identified patent and that said Letters Patent is hereby corrected as shown below:

Title page, (73), please replace the Assignee Name, "InClone Systems, Incorporated, New York, NY (US)" with -- ImClone Systems, Incorporated, New York, NY (US)--

Claim 10, column 20, line 9: replace "CD34+" with --$CD34^+$--

Claim 11, column 20, line 11: replace "CD34+" with --$CD34^+$--

Signed and Sealed this

Twelfth Day of December, 2006

JON W. DUDAS
*Director of the United States Patent and Trademark Office*